United States Patent
Huang et al.

(10) Patent No.: US 11,591,299 B1
(45) Date of Patent: Feb. 28, 2023

(54) PRODRUG COMPOUND OF LEVOSIMENDAN, PREPARATION METHOD AND USE THEREOF

(71) Applicant: Beijing Chenguang Tongchuang Pharmaceutical Research Institute Co., Ltd., Beijing (CN)

(72) Inventors: Shaolin Huang, Beijing (CN); Changbin Guo, Beijing (CN); Wei Li, Beijing (CN); Liang Ma, Beijing (CN); Qingjuan Yang, Beijing (CN); Pengfei Song, Beijing (CN); Jingwang Fan, Beijing (CN); Xiaosong Mao, Beijing (CN)

(73) Assignee: Beijing Chenguang Tongchuang Pharmaceutical Research Institute Co., Ltd., Beijing (CN)

( * ) Notice: Subject to any disclaimer, the term of this patent is extended or adjusted under 35 U.S.C. 154(b) by 0 days.

(21) Appl. No.: 17/695,335

(22) Filed: Mar. 15, 2022

(51) Int. Cl.
*C07D 237/04* (2006.01)

(52) U.S. Cl.
CPC ................................. *C07D 237/04* (2013.01)

(58) Field of Classification Search
CPC .................................................. C07D 237/04
See application file for complete search history.

(56) References Cited

FOREIGN PATENT DOCUMENTS

| CN | 1626085 A | 6/2005 |
| CN | 108261398 A | 7/2018 |
| WO | 2017037737 A1 | 3/2017 |

*Primary Examiner* — Golam M Shameem
(74) *Attorney, Agent, or Firm* — Scully, Scott, Murphy & Presser, P.C.

(57) ABSTRACT

The invention relates to a prodrug compound of levosimendan as shown by the formula below, and solvates, hydrates, N-oxides, stereoisomers, and pharmaceutically acceptable salts thereof, wherein each of Ra and Rb is selected from hydrogen or C1-C6 alkyl; Rp is selected from a basic group containing N atom or an acidic group containing carboxyl group, phosphate group, sulfate group, and sulfonate group. The prodrug compound overcomes the defects of levosimendan such as poor water solubility, and has an ideal pharmacokinetic profile and excellent prospects for medicament development.

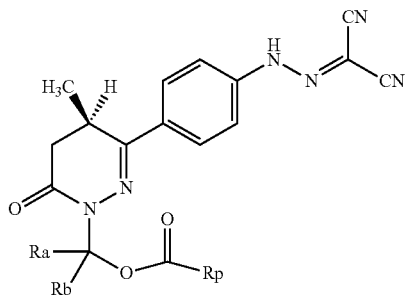

8 Claims, 4 Drawing Sheets

PRODRUG COMPOUND OF LEVOSIMENDAN, PREPARATION METHOD AND USE THEREOF

TECHNICAL FIELD

The invention relates to a prodrug compound of levosimendan, preparation method and use thereof, and belongs to the fields of chemical synthesis and medicine.

BACKGROUND

Acute heart failure (HF) refers to the rapid onset or deterioration of symptoms and signs of heart failure, mainly manifested as a clinical syndrome of a series of symptoms like decreased myocardial contractility, decreased cardiac output, increased pulmonary circulation pressure, increased peripheral circulatory resistance, and insufficient perfusions of tissues and organs. The annual mortality of acute heart failure in China is as high as 34% (Analysis of recent prognosis of elderly patients with acute decompensated heart failure and its influencecing factors, China Medical Herald, 2017, 14(14): 52-55).

According to "Guidelines for primary diagnosis and treatment of acute heart failure (2019)", acute heart failure needs to be treated with positive inotropic drugs, diuretics, vasodilators and other drugs. The commonly used inotropes include calcium sensitizers (such as Levosimendan), beta-adrenergic receptor agonists (such as Dobutamine), phosphodiesterase inhibitors (such as Milrinone), etc. (Guidelines for primary diagnosis and treatment of acute heart failure (2019), Chinese Journal of General Practitioners, 2019, 10, 925-930).

Levosimendan is mainly used for treating various acute heart failure conditions in clinic. It was developed by Orion (Finland) and first marketed in Sweden in October 2000. Its chemical name is (R)-[[4-(1,4,5,6-tetrahydro-4-methyl-6-oxo-pyridazin-3-yl)phenyl]-hydrazono]-malononitrile, with a molecular formula of $C_{14}H_{12}N_6O$ and a molecular weight of 280.28 (CAS. NO. 131741-08-7), and its chemical structure is shown by the formula below:

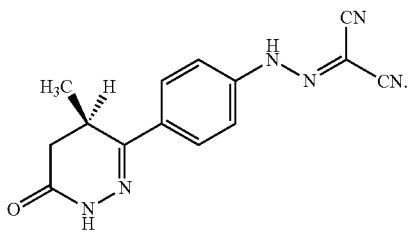 [SMILES: C[C@@H]1CC(=O)NN=C1c1ccc(NN=C(C#N)C#N)cc1]

As a multi-targeted drug, the main action mechanism of levosimendan in the treatment of acute heart failure can be summarized in two aspects: firstly, as a calcium ion sensitizer, levosimendan can exert a positive inotropic effect on cadiocytes by enhancing the sensitivity of cardiac fibrous troponin C to calcium ions, without increasing the concentration of calcium ions in cadiocytes; and secondly, levosimendan can open ATP-dependent potassium channels ($K_{ATP}$) on cadiocytes and vascular smooth muscle cells, causing hyperpolarization of vascular smooth muscle cells, dilating coronary arteries and peripheral blood vessels, and reducing the circulatory system resistance. In addition, levosimendan has a weak inhibitory effect on phosphodiesterase-III (PDE-III), increasing the concentration of cyclic adenosine monophosphate (cAMP) in cadiocytes and thereby increasing the concentration of intracellular calcium ions to a certain extent. However, studies have shown that this mechanism does not have a significant effect in a clinically effective therapeutic range.

Traditional therapeutic drugs for heart failure, such as dobutamine and milrinone, all exert positive inotropic effects by improving the concentration of cAMP through different mechanisms and thereby increasing the concentration of intracellular calcium ions. Levosimendan exerts a positive inotropic effect through a calcium ion sensitization mechanism and does not increase myocardial energy consumption, because it does not act through the mechanism of intramolecular calcium ion increase or intermolecular calcium ion migration. Moreover, studies have shown that levosimendan has unique cardioprotective effects, which can bring about long-term beneficial hemodynamic and energy balance effects to patients. These characteristics make levosimendan more advantageous than traditional therapeutic drugs for heart failure (Levosimendan in Cardiac Surgery: Evaluating the Evidence. Journal of Cardiothoracic and Vascular Anesthesia, 2019, 33, 1146-1158).

Since levosimendan has poor solubility and stability in water, it is of great significance to study how to improve its water solubility. The current clinical dosage form is an injection solution made by the solution of levosimendan in sterile anhydrous ethanol in which the addition of co-solvent is required. The original manufacturer uses povidone K12 as the co-solvent, and the generic drug manufacturers in China use polyethylene glycol PEG400 or hydroxypropyl-β-cyclodextrin as the co-solvent. In addition, there are several patent literatures reporting that the use of co-solvent improves the water-solubility of levosimendan, for example using substituted cyclodextrin as a solubilizer (Levosimendan-containing pharmaceutical formulation for injection and preparation method thereof, Chinese Invention Patent Publication (Announcement) No.: 108261398A; Levosimendan freeze-dried formulation and preparing method, Chinese Invention Patent Publication (Announcement) No.: 1626085A); using polyvinylpyrrolidone as a solubilizer (Parenteral formulations of levosimendan, International patent application WO 2017037737A1); using povidone K12PF as a solubilizer (Levosimendan-containing pharmaceutical formulation for injection and preparation method thereof, Chinese Invention Patent Publication (Announcement) No.: 108261398A), etc.

The use of non-aqueous solvents and co-solvents to solve the problem of poor water solubility of drugs is not an ideal solution. For patients with acute heart failure, the introduction of absolute ethanol into the circulatory system will definitely bring about adverse effects and side effects. The aforementioned co-solvents, such as povidone K12, tend to bring about unwanted side effects.

Thus, it is clinically necessary to develop a compound derived from levosimendan, which can effectively solve the solubility problem, and has a simple manufacturing method, thereby reducing the technical disadvantage of inconveniences caused by insolubility and instability of levosimendan itself in water.

SUMMARY

In view of the above technical problems, the inventors provide a prodrug compound of levosimendan, wherein the compound is a compound having the structure shown in general formula I, and solvates, hydrates, N-oxides, stereoisomers, and pharmaceutically acceptable salts thereof;

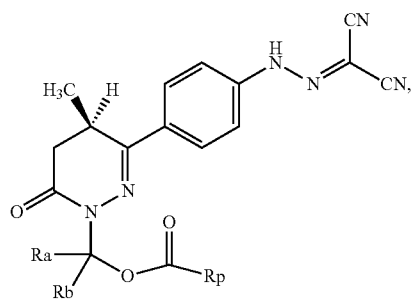

I wherein each of Ra and Rb is selected from hydrogen atom or C1-C6 alkyl;

Rp is selected from a basic group containing N atom, or an acidic group containing carboxyl, phosphate group, sulfate group, and sulfonate group.

The basic group containing N atom is a basic group that can form a salt with an inorganic acid or an organic acid. The acidic group is an acidic group that can form a salt with an inorganic base or an organic base.

Each of Ra and Rb is preferably hydrogen atom.

Technically, levosimendan is insoluble in water and is extremely difficult to form salts, so the solubility problem cannot be solved by salifying. The prodrug molecules provided by the invention have water-soluble substituents, and the water-soluble substituents are not casually incorporated, but must have the following characteristics:

1. The synthesis operator can synthesize and obtain the molecule;

2. The molecule has an excellent water solubility or a property of forming soluble salts with other acids, bases, or organic solvents;

3. It has the characteristics of a prodrug molecule, that is, it can be rapidly metabolized in vivo to form levosimendan;

4. It has a common parent ring structure, and when the corresponding substituent is cleaved, it has no toxic and side effects during in vivo metabolism.

Thus, in order to seek compound molecules satisfying these three conditions, the inventors have explored on the basis of years of drug research experiences and in combination with the existing technology, to screen out the following types of substituents and parent ring structures, namely formula I.

Firstly, in the structural formula of levosimendan, —CH$_2$—O— moiety is connected to the —N at position 1 of the tetrahydropyridazinone ring. This moiety connected to other substituents can be rapidly cleaved during in vivo metabolism and converted into levosimendan with a high conversion rate. Secondly, the substituents must be subjected to the experimental validation and will not bring about any additional side effects upon metabolism.

Thus, for the substituent, the basic group containing N atom is selected from 4-(morpholin-1-ylmethyl)phenyl, 4-(4-methylpiperazin-1-ylmethyl)phenyl, N,N-dimethylaminomethyl, pyridin-3-yl, 4-(piperidin-1-yl)-piperidin-1-yl, aminomethyl, pyridin-4-ylmethylaminoformylmethyl, or pyrrolidin-1-ylmethyl.

Preferably, the acidic group is selected from carboxylmethyl, carboxylethyl, carboxylmethoxy, phosphoryloxymethyl, sulfonyloxymethyl, sulfonylmethyl, phosphoryloxyethyl, sulfonyloxyethyl, or sulfonylethyl.

At present, there is no research on the prodrugs for levosimendan. The invention has developed a series of above-mentioned compounds. Firstly, in view of the technical problem of poor water solubility of levosimendan, the inventors have introduced some solubilizing groups with specific structures, such that all the compounds have the structure of above general formula I.

Structurally, in present invention, a substituent is introduced at the 1-position N of the tetrahydropyridazinone ring in the structural formula of levosimendan. As determined by early experiments, the compound has the following characteristics, as compared to those with side chain(s) introduced at other sites:

1) The preparation method is simple; and

2) The introduced side chain can be successfully subjected to the covalent bond cleavage between N—CH$_2$ to form the original drug levosimendan, which contributes to improving the decomposition activity of the prodrug.

A series of compounds are preferably selected by the inventors, including the structural formulae with Rp group names and chemical names below (see Table 1).

TABLE 1

Structural formulae and chemical names of preferred compounds

| No. | Structural formula | No. | Structural formula |
|---|---|---|---|
|  | First subtype |  | The acyl moiety carries a basic group containing N atom, which can form an acid salt. |

1

Rp = 4-(morpholin-1-ylmethyl)phenyl
Chemical name: (R)-(3-((4-(2-(dicyanomethylene)hydrazino)phenyl)-4-methyl-6-oxo-5,6-dihydropyridazin-1(4H)-yl)methyl 4-(morpholin-1-ylmethyl)benzoate
(TCX-1001-031)
This product is sparingly soluble in water

2

Rp = 4-(4-methylpiperazin-1-ylmethyl)phenyl
Chemical name: (R)-(3-((4-(2-(dicyanomethylene)hydrazino)phenyl)-4-methyl-6-oxo-5,6-dihydropyridazin-1(4H)-yl)methyl 4-((4-methylpiperazin-1-yl)methyl)benzoate
(TCX-1001-033)
This product is sparingly soluble in water

3

Rp = N,N-dimethylaminomethyl
Chemical name: (R)-(3-((4-(2-(dicyanomethylene)hydrazino)phenyl)-4-methyl-6-oxo-5,6-dihydropyridazin-1(4H)-yl)m ethyl N,N-dimethylglycinate
(TCX-1001-030)
This product is slightly soluble in water

4

Rp = pyridin-3-yl
Chemical name: (R)-(3-((4-(2-(dicyanomethylene)hydrazino)phenyl)-4-methyl-6-oxo-5,6-dihydropyridazin-1(4H)-yl)methyl nicotinate
(TCX-1001-029)
This product is extremely slightly soluble in water TABLE 1-continued Structural formulae and chemical names of preferred compounds

| No. | Structural formula | No. | Structural formula |
|---|---|---|---|
| 5 | Rp = 4-(piperidin-1-yl)-piperidin-1-yl<br>Chemical name: (R)-(3-((4-(2-(dicyanomethylene)hydrazino)phenyl)-4-methyl-6-oxo-5,6-dihydropyridazin-1(4H)-yl)methyl 4-(piperidin-1-yl)piperidin-1-ylformate<br>(TCX-1001-037)<br>This product is sparingly soluble in water | 6 | Rp = aminomethyl<br>Chemical name: (R)-(3-((4-(2-(dicyanomethylene)hydrazino)phenyl)-4-methyl-6-oxo-5,6-dihydropyridazin-1(4H)-yl)m ethyl glycinate<br>(TCX-1001-032)<br>This product is slightly soluble in water |
| 7 | Rp = pyridin-4-ylmethylaminoformylmethyl<br>Chemical name: (R)-(3-((4-(2-(dicyanomethylene)hydrazino)phenyl)-4-methyl-6-oxo-5,6-dihydropyridazin-1(4H)-yl)methyl 3-oxo-3-((pyridin-4-ylmethyl)amino)propionate<br>(TCX-1001-036)<br>This product is extremely slightly soluble in water | 8 | Rp = pyrrolidin-1-ylmethyl<br>Chemical name: (R)-(3-((4-(2-(dicyanomethylene)hydrazino)phenyl)-4-methyl-6-oxo-5,6-dihydropyridazin-1(4H)-yl)methyl 2-pyrrolidin-1-yl-acetate<br>(TCX-1001-03 9)<br>This product is slightly soluble in water |

TABLE 1-continued

Structural formulae and chemical names of preferred compounds

| No. | Structural formula | No. | Structural formula |
|---|---|---|---|
| | Second subtype | | The acyl moiety carries an acidic group |

1 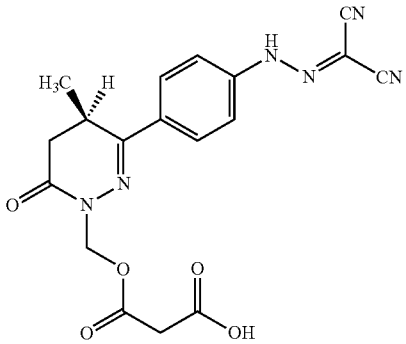 [SMILES: C[C@@H]1CC(=O)N(COC(=O)CN(C)C)N=C1c1ccc(NN=C(C#N)C#N)cc1]

Rp = carboxylmethyl
Chemical name: (R)-(3-((4-(2-(dicyanomethylene)hydrazino)phenyl)-4-methyl-6-oxo-5,6-dihydropyridazin-1(4H)-yl)methyl 2-carboxylacetate
(TCX-1001-041)
This product is slightly soluble in water 2 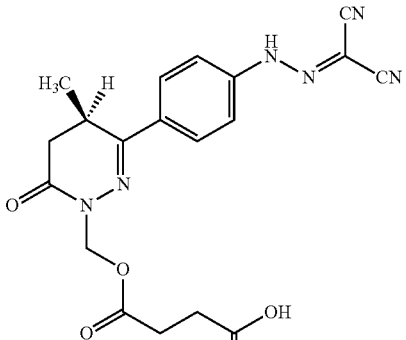

Rp = carboxyl ethyl
Chemical name: (R)-(3-((4-(2-(dicyanomethylene)hydrazino)phenyl)-4-methyl-6-oxo-5,6-dihydropyridazin-1(4H)-yl)methyl 3-carboxylpropionate
(TCX-1001-034)
This product is slightly soluble in water 3 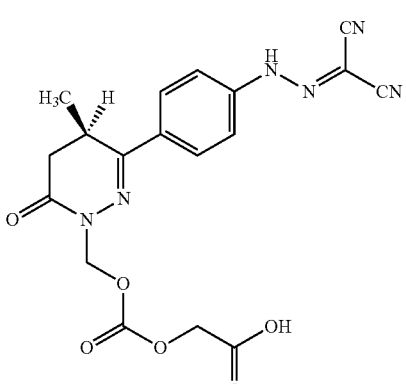

Rp = carboxylmethoxy
Chemical name: (R)-((4-(2-(dicyanomethylene)hydrazino)phenyl)-4-methyl-6-oxo-5,6-dihydropyridazin-1(4H)-yl)methyl carboxylmethyloxyformate
(TCX-1001-035)
This product is slightly soluble in water 4 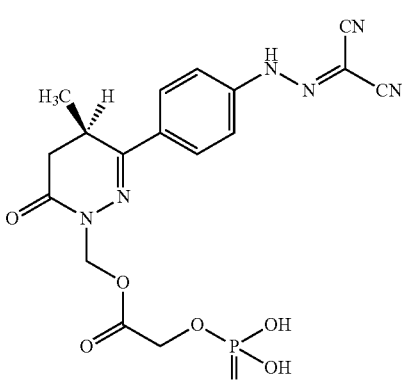

Rp = phosphoryloxymethyl
Chemical name: (R)-(3-((4-(2-(dicyanomethylene)hydrazino)phenyl)-4-methyl-6-oxo-5,6-dihydropyridazin-1(4H)-yl)methyl phosphoryloxyacetate
(TCX-1001-040)
This product is extremely soluble in water TABLE 1-continued Structural formulae and chemical names of preferred compounds

| No. | Structural formula | No. | Structural formula |
|---|---|---|---|
| 5 | (structure shown) | | |

Rp = sulfonyloxymethyl
Chemical name: (R)-(3-((4-(2-(dicyanomethylene)hydrazino)phenyl)-4-methyl-6-oxo-5,6-dihydropyridazin-1(4H)-yl)methyl sulfonyloxyacetate
(TCX-1001-038)
This product is extremely soluble in water After the above structure is formed, the water solubility of the prodrug molecule can be significantly improved. Levosimendan is not only insoluble in water, but also insoluble or extremely poorly soluble in most organic solvents, while the water solubility of the levosimendan prodrug compounds provided by the inventors ranges from extremely slightly soluble to extremely soluble.

Solubility Determination

The determination is based on the solubility test method in General Example 15 of Part IV in "Chinese Pharmacopoeia (2020 Edition)": the test product was ground into fine powders, and water at about 25° C. is added in a certain water bath at 25° C.±2° C., and shaken vigorously for 30 seconds every 5 minutes, to observe the dissolution within 30 minutes. If there are no visible solute particles, it is regarded as complete dissolution.

TABLE 2

Definition of Solubility

| | |
|---|---|
| Extremely soluble | It means that 1 g (ml) of solute can be dissolved in less than 1 ml of solvent |
| Easily soluble | It means that 1 g (ml) of solute can be dissolved in 1 ml to less than 10 ml of solvent |
| Soluble | It means that 1 g (ml) of solute can be dissolved in 10 ml to less than 30 ml of solvent |
| Sparingly soluble | It means that 1 g (ml) of solute can be dissolved in 30 ml to less than 100 ml of solvent |
| Slightly soluble | It means that 1 g (ml) of solute can be dissolved in 100 ml to less than 1000 ml of solvent |
| Extremely slightly soluble | It means that 1 g (ml) of solute can be dissolved in 1000 ml to less than 10000 ml of solvent |
| Barely soluble or insoluble | It means that 1 g (ml) of solute cannot be completely dissolved in 10000 ml of solvent |

According to the current researches on levosimendan, levosimendan can hardly be salified (whether inorganic or organic acid or base is added), and its solubilities in most solvents (including organic solvents and water) are extremely poor. Thus, the currently marketed levosimendan formulations are all injections made by dissolving in organic solvents (the organic solvent selected for the commercial product is absolute ethanol), wherein it is also required to add a co-solvent (the co-solvent selected for the current commercial product is povidone K12 with a relatively higher toxicity), so as to prepare the formulation. In general, due to the solubility defect of levosimendan, the introduction of organic solvent as a solvent and the addition of co-solvent to make the formulation are likely to bring about toxicity or side effects, resulting in drug safety events.

The present invention can firstly synthesize the prodrug molecule of levosimendan, which belongs to the first synthesis, and it is a molecule directly having a solubility between extremely slight dissolution and extreme dissolution. Moreover, the substituent of the prodrug molecule has the characteristics of a basic group containing N atom or an acidic group containing carboxyl, phosphate group, sulfate group, or sulfonate group. It is easy to form a salt in water, or by adding an acid-base regulator (strong acid, strong base, weak acid, weak base, pH regulator with stabilizing effect, etc.), the purpose of easier dissolution could be achieved. Thus, the levosimendan prodrug molecule prepared by the invention represents a landmark in its pharmaceutical prospect.

The invention solves the problem of poor solubility of levosimendan in most solvents (including water). When preparing a liquid formulation of levosimendan, the defects of having to use an organic solvent and adding a toxic co-solvent at the same time are avoided.

Meanwhile, due to its solubility limitation, levosimendan itself cannot be dispersed in gastric juice and intestinal juice, so it is difficult to make oral formulations. The novel compounds designed and prepared in the invention overcomes this defect and can be dispersed in water, that is, they can be dispersed in gastric juice or intestinal juice in the form of molecules or ions, which is beneficial to the oral absorption in organisms, and solves the problem that it is difficult to prepare levosimendan into oral formulations.

In addition, the metabolic behavior of the compound designed and prepared in the invention (converted into levosimendan in human body) can be used for the preparation of a controlled-release formulation that is more suitable for exerting the efficacy of levosimendan.

These characteristics will lead to great clinical values and commercial values of the invention.

Unless otherwise specified, these terms have the following meanings.

The term "alkyl" means a straight or branched alkyl having 1 to 6 carbons.

The term "pharmaceutically acceptable salt" means a pharmaceutically acceptable acid or a base addition salt. The compounds of formula (I) having basic properties can be converted to their pharmaceutically acceptable acid addition salts by treating with an appropriate acid. Suitable acids include, for example, inorganic acids such as halogen acids such as hydrochloric acid or hydrobromic acid; sulfuric acid; nitric acid; phosphoric acid; or organic acids such as acetic acid, propionic acid, glycolic acid, lactic acid, pyruvic acid, oxalic acid, malonic acid, succinic acid, maleic acid, fumaric acid, malic acid, tartaric acid, citric acid, methanesulfonate, ethanesulfonate, benzenesulfonate, p-toluenesulfonate, cyclohexylaminosulfonate, salicylic acid, p-aminosalicylic acid, and pamoic acid. The compounds of formula (I) having acidic properties can be converted into their pharmaceutically acceptable base addition salts by treating said acid form with a suitable organic or inorganic base. Suitable base salt forms include, for example, ammonium, alkali and alkaline earth metal salts, such as lithium, sodium, potassium, magnesium, calcium salts, etc., salts with organic bases, such as N,N'-bisbenzylethylenediamine salts, N-methyl-D-glucosamine salts, diethylamine salts, diethanolamine salts, and salts with amino acids such as for example salts with arginine, lysine, and the like.

The invention can also relate to the preparation of a formulation, which is prepared from an effective dose of the compound of the invention and a pharmaceutically acceptable adjuvant. The pharmaceutically acceptable adjuvant refers to the adjuvant required to make any pharmaceutical dosage form suitable for human or animal use. For example, when making oral solid formulations, the pharmaceutically acceptable adjuvant refers to diluents, binders, wetting agents, disintegrants, lubricants, and glidants; and when making injections, the pharmaceutically acceptable adjuvant refers to pH adjusters, co-solvents, antioxidants, isotonic agents, etc.

Preferably, the basic group containing N atom is selected from 4-(morpholin-1-ylmethyl)phenyl, 4-(4-methylpiperazin-1-ylmethyl)phenyl, N,N-dimethylaminomethyl, or pyridin-3-yl.

Further preferably, the basic group containing N atom is selected from 4-(morpholin-1-ylmethyl)phenyl or 4-(4-methylpiperazin-1-ylmethyl)phenyl.

The invention provides a method for preparing the above compound, including the following steps:

(1) di-tert-butyl dicarbonate is reacted with (R)-6-((4-aminophenyl)-5-methyl-4,5-dihydropyridazin-3(2H)-one, to obtain tert-butyl (R)-(4-((4-methyl-6-oxo-1,4,5,6-tetrahydropyridazin-3-yl)phenyl)carbamate;

(2) tert-butyl (R)-(4-((4-methyl-6-oxo-1,4,5,6-tetrahydropyridazin-3-yl)phenyl)carbamate is reacted with paraformaldehyde in the presence of a base, to obtain tert-butyl (R)-(4-(1-(hydroxymethyl)-4-methyl-6-oxo-1,4,5,6-tetrahydropyridazin-3- yl)phenyl)carbamate;

(3) under an acidic condition, the Boc group is removed from tert-butyl (R)-(4-(1-(hydroxymethyl)-4-methyl-6-oxo-1,4,5,6-tetrahydropyridazin-3- yl)phenyl)carbamate, to convert to (R)-6-((4-aminophenyl)-2-(hydroxymethyl)-5-methyl-4,5-dihydropyridazin-3 (2H)-one;

(4) under an acidic condition, (R)-6-((4-aminophenyl)-2-(hydroxymethyl)-5-methyl-4,5-dihydropyridazin-3(2H)-one is reacted with sodium nitrite and malononitrile, to obtain (R)-N-((4-(1-(hydroxymethyl)-4-methyl-6-oxo-1,4,5,6-tetrahydropyridazin-3- yl)phenyl)biscyanomethylene) hydrazine;

(5) (R)-N-((4-(1-(hydroxymethyl)-4-methyl-6-oxo-1,4,5, 6-tetrahydropyridazin yl)phenyl)biscyanomethylene)hydrazine prepared in step (4) is reacted with the carboxylic acid having the corresponding substituent or its activated form respectively, to obtain the prodrug compound.

The synthetic route is shown in the following scheme:

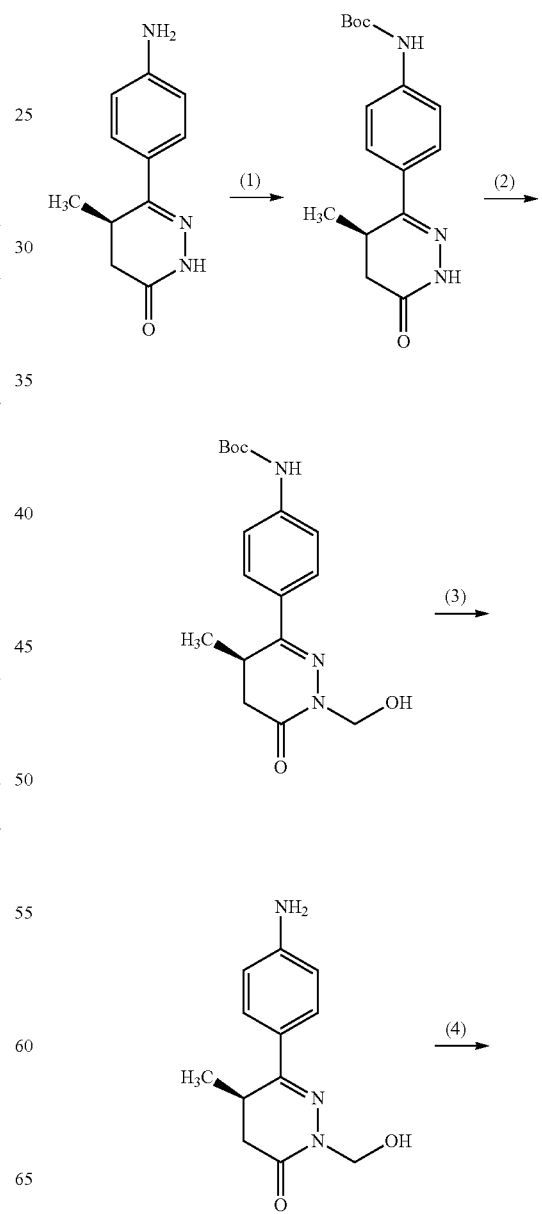

15

-continued

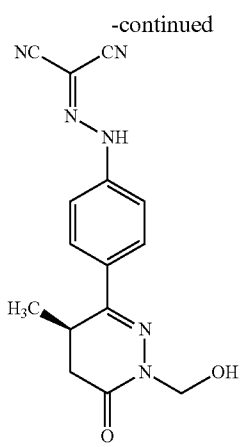

(5) →

16

-continued

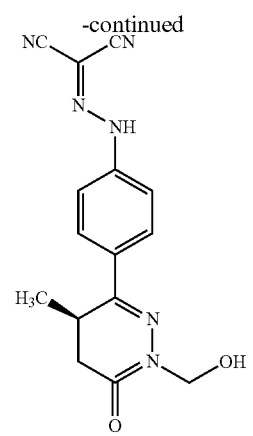

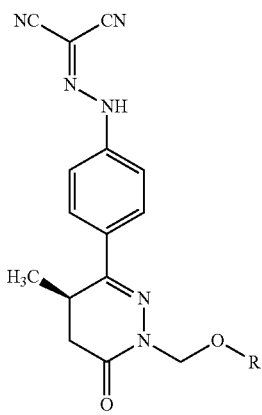

In the above preparation method, the invention also provides the use of intermediates tert-butyl (R)-(4-(1-(hydroxymethyl)-4-methyl-6-oxo-1,4,5,6-tetrahydropyridazin-3-yl)phenyl)carbamate, (R)-6-((4-aminophenyl)-2-(hydroxymethyl)-5-methyl-4,5-dihydropyridazin-3(2H)-one, and (R)-N-((4-(1-(hydroxymethyl)-4-methyl-6-oxo-1,4,5,6-tetrahydropyridazin-3-yl)phenyl)biscyanomethylene)hydrazine in the above steps (2), (3), and (4) in the manufacture of a medicament for treating heart failure diseases.

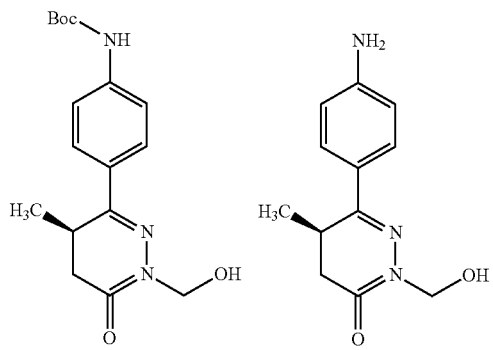

The invention provides a method for preparing a compound of general formula I, consisting of the following steps:

(1) Preparation of tert-butyl (R)-(4-((4-methyl-6-oxo-1,4,5,6-tetrahydropyridazin-3-yl)phenyl)carbamate (R)-6-((4-aminophenyl)-5-methyl-4,5-dihydropyridazin-3(2H)-one, di-tert-butyl dicarbonate, triethylamine, and tetrahydrofuran are added to a container, and stirred at room temperature for 1-5 days. After no remaining raw materials were detectable by TLC detection, it is filtered, and subjected to rotary evaporation under reduced pressure to remove the solvent. To the concentrate petroleum ether is added, pulped at room temperature for 10-60 minutes, and filtered. The resulting solid is dried, to obtain a light brown solid.

(2) Preparation of tert-butyl (R)-(4-(1-(hydroxymethyl)-4-methyl-6-oxo-1,4,5,6-tetrahydropyridazin-3-yl)phenyl)carbamate Tert-butyl (R)-(4-((4-methyl-6-oxo-1,4,5,6-tetrahydropyridazin-3-yl)phenyl)carbamate obtained in step (1) and methanol are added to a container, paraformaldehyde and potassium carbonate are added under stirring, and stirred at room temperature until the completed reaction by TLC monitoring. The solvent is removed by rotary evaporation under reduced pressure. The concentrate is purified by column chromatography, using a mixed solvent of petroleum ether and ethyl acetate (v:v 1:1) as the eluent, to obtain a white solid.

(3) Preparation of (R)-6-((4-aminophenyl)-2-(hydroxymethyl)-5-methyl-4,5-dihydropyridazin-3(2H)-one hydrochloride Tert-butyl (R)-(4-((4-methyl-6-oxo-1,4,5,6-tetrahydropyridazin-3-yl)phenyl)carbamate obtained in step (2) is added to a container and ethyl acetate is added. After stirring at room temperature for 1-10 minutes, a solution of hydrogen chloride in ethyl acetate is dropwise added. After dropwise addition is completed, the reaction is stirred at room temperature until no remaining raw materials detectable by TLC detection. The solvent is removed by concentration under reduced pressure, to obtain crude (R)-6-((4-aminophenyl)-2-(hydroxymethyl)-5-methyl-4,5-dihydropyridazin-3(2H)-one hydrochloride, as a yellow solid, which is directly subjected to in the next reaction.

(4) Preparation of (R)-N-((4-(1-(hydroxymethyl)-4-methyl-6-oxo-1,4,5,6-tetrahydropyridazin-3-yl)phenyl)biscyanomethylene)hydrazine Crude (R)-64(4-aminophenyl)-2-(hydroxymethyl)-5-methyl-4,5-dihydropyridazin-3 (2H)-one hydrochloride obtained in step (3) is transferred into a container with an aqueous hydrochloric acid solution. At 5 to 10° C. controlled with an ice-water bath, an aqueous solution of sodium nitrite is added to the above reaction solution. After addition, the stirring is continued for 10 minutes to 2 hours in the ice-water bath. At 5 to 10° C., an aqueous solution of malononitrile is added to the above reaction solution. After addition, the ice-water bath is removed. After stirring at room temperature for 1-5 hours, an aqueous solution of sodium acetate is slowly added, to adjust pH value to be from 5 to 6. A yellow suspension is obtained, filtered, washed with water, and dried, to obtain a yellow solid.

(5) Preparation of the Compound of General Formula I (R)-N-((4-(1-(hydroxymethyl)-4-methyl-6-oxo-1,4,5,6-tetrahydropyridazin yl)phenyl)biscyanomethylene)hydrazine prepared in step (4) is esterified with a carboxylic acid having the corresponding substituent or its activated form respectively, to obtain the compound of general formula.

All the compounds of the invention not only have a general structure, but also can be prepared from a common intermediate (R)-N-((4-(1-(hydroxymethyl)-4-methyl-6-oxo-1,4,5,6-tetrahydropyridazin-3-yl)phenyl)biscyanomethylene)hydrazine through esterification; that is, through the preparation of anterior intermediate, subsequent compounds with various substituents can be prepared through esterification with the carboxylic acid having the corresponding substituents or its activated form. Thus, the preparation route of this preparation method is mainly to firstly prepare the intermediate, and then carry out esterification to synthesize various specific compounds as the prodrug compounds.

In the above preparation method, in step (5), the compound (R)-N-((4-(1-(hydroxymethyl)-4-methyl-6-oxo-1,4,5,6-tetrahydropyridazin-3- yl)phenyl)biscyanomethyl)hydrazino, TSTU, and carboxylic acid substituted by various Rp groups are added to a container and dichloromethane is added, then triethylamine is added under stirring, and stirred at room temperature for 1-10 hours. After no remaining raw materials were detectable by TLC detection, the solvent is removed by rotary evaporation under reduced pressure. The resulting concentrate is purified by column chromatography, using the mixed solvent of dichloromethane and methanol (v:v 50:1) as the eluent, to obtain a prodrug compound of levosimendan.

The invention further provides the use of the above-mentioned prodrug compounds in the manufacture of a medicament for treating heart failure diseases.

Advantageous Effects

The invention provides a prodrug compound of levosimendan. In the structural formula of levosimendan, N at 1-position of the tetrahydropyridazinone ring is correspondingly substituted, solving the problem that the water solubility of levosimendan is extremely poor. Moreover, this prodrug compound has the characteristics such as good stability, easier drug metabolism, and convenient use. It is no longer necessary to use absolute ethanol as a solvent and other co-solvents in the formulation, thus greatly facilitating the clinical use. This prodrug compound of levosimendan can be rapidly converted into levosimendan in vivo, with a high conversion rate and good drug-forming properties. According to the obtained pharmacokinetic data, it can be concluded that the compounds provided by the invention can be used as levosimendan prodrugs. These compounds also have the advantage of pharmacokinetically controlling the release rate of levosimendan in vivo. Additionally, it can also solve the problem that levosimendan is not suitable for oral administration.

Abbreviation Definitions

TSTU: 2-succinimidyl -1, 1,3,3-tetramethylurea tetrafluoroborate;
TLC: thin layer chromatography;
$^1$H-NMR: H nuclear magnetic resonance spectrum;
TMS: tetramethylsilane
DMSO-$d_6$: hexadeuterated dimethyl sulfoxide;
ESI-MS: electrospray ionization-mass spectrometry;
$K_{ATP}$: ATP-dependent potassium channel;
PDE-III: phosphodiesterase-III;
cAMP: cyclic adenosine monophosphate;
PEG: polyethylene glycol;
DCM: dichloromethane;
MtOH: methanol;
DMF: N,N-dimethylformamide.

DESCRIPTION OF EMBODIMENTS

Figure 1:
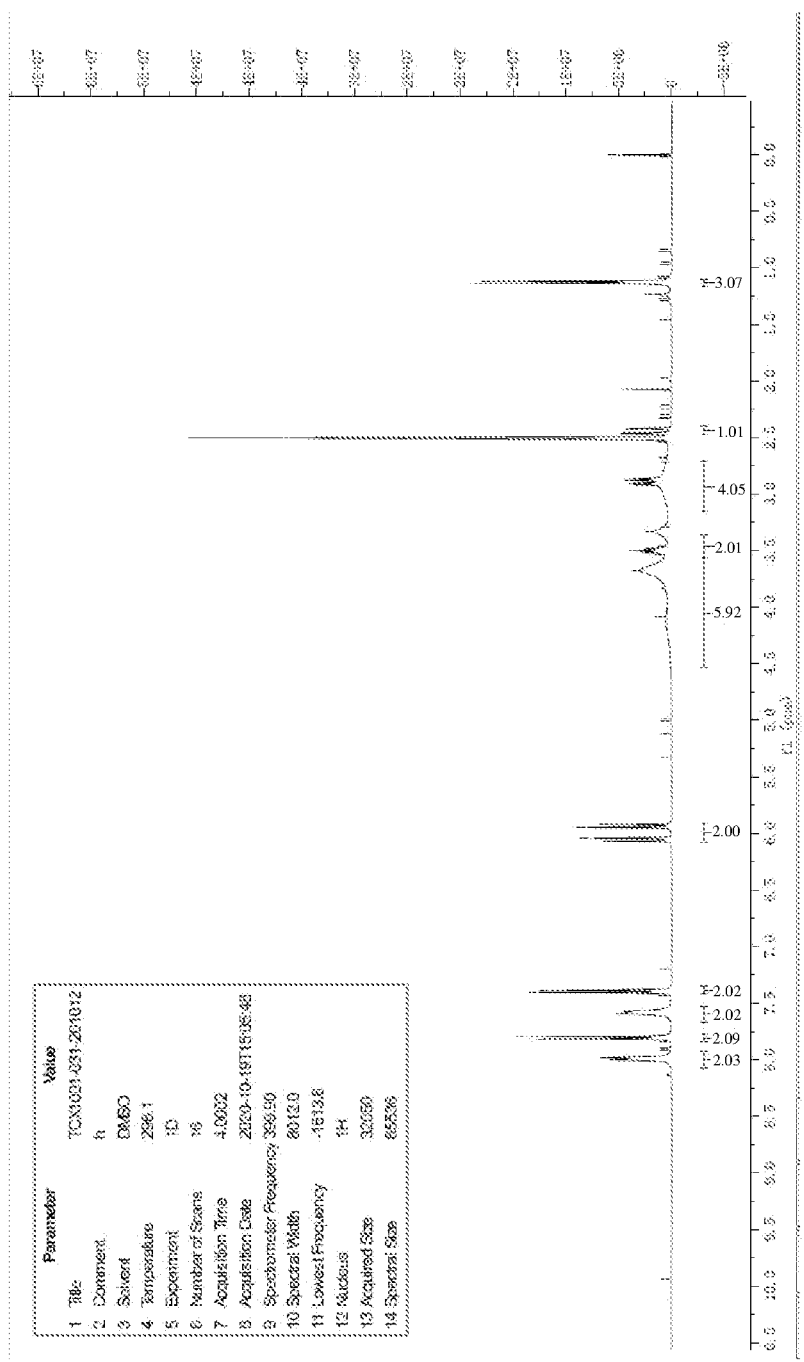
FIG. 1 $^1$H-NMR spectrum of compound TCX1001-031.

The embodiments of the invention and the beneficial effects produced will be described in detail below through specific examples, which are intended to help readers better understand the essences and characteristics of the invention, and are not intended to limit the scope of present invention.

The structures of the compounds are characterized by H nuclear magnetic resonance ($^1$HNMR) and/or mass spectrometry (MS). $^1$HNMR is determined with Bruker Spectrometer AVIII HD NMR spectrometer (400 MHz), and the chemical shifts (δ) are given in $10^{-6}$ (ppm). The internal standard is tetramethylsilane (TMS). Chemical shift: δ, s: singlet; d: doublet; t: triplet; q: quartet; m: multiplet. Mass spectra is determined with Agilent Accurate-Mass Q-TOF LC/MS mass spectrometer.

Unless otherwise specified, benzyl carbazate is purchased from Shanghai Haohong Biomedical Technology Co., Ltd.; paraformaldehyde is purchased from Shanghai Macklin Biochemical Co., Ltd., diethyl phosphate is purchased from Shanghai Macklin Biochemical Co., Ltd.; 2,2-diethoxyethyl diethyl phosphate is purchased from Alfa Aesar (China) Chemical Co., Ltd.; tert-butoxycarbonylhydrazine is purchased from Shanghai Bide Pharmaceutical Technology Co., Ltd.; (R)-6-((4-aminophenyl)-5-methyl-4,5-dihydropyridazin-3(2H)-one is homemade in Beijing Chenguang Tongchuang Pharmaceutical Research Institute Co., Ltd. TLC refers to thin layer chromatography; TSTU refers to O-(N-succinimidyl)-N N N'N'-tetramethyltetrafluoroborate urea; DCM refers to dichloromethane; MtOH refers to methanol; DMF refers to dimethylformamide. The specifications of petroleum ether used are in the boiling range of 60-90° C.
The synthesis route for N-((4-(1-(hydroxymethyl)-4-methyl-6-oxo-1,4,5,6-tetrahydropyridazin-3-yl)phenyl)bis-cyanomethylene)hydrazine (5) as the common intermediate is as follows:
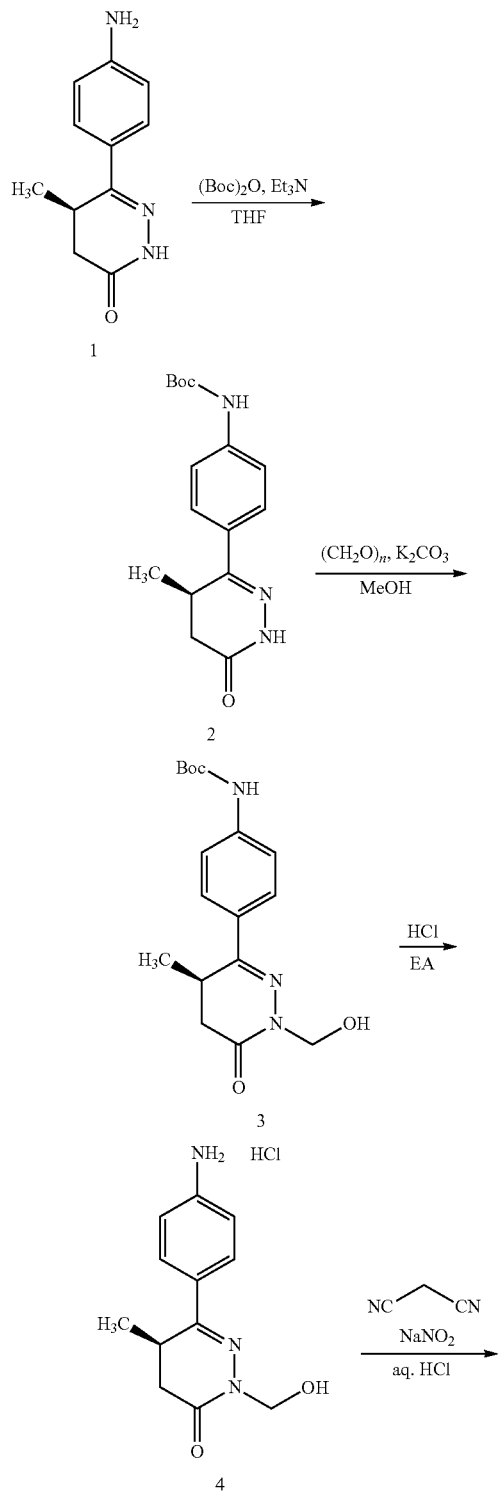
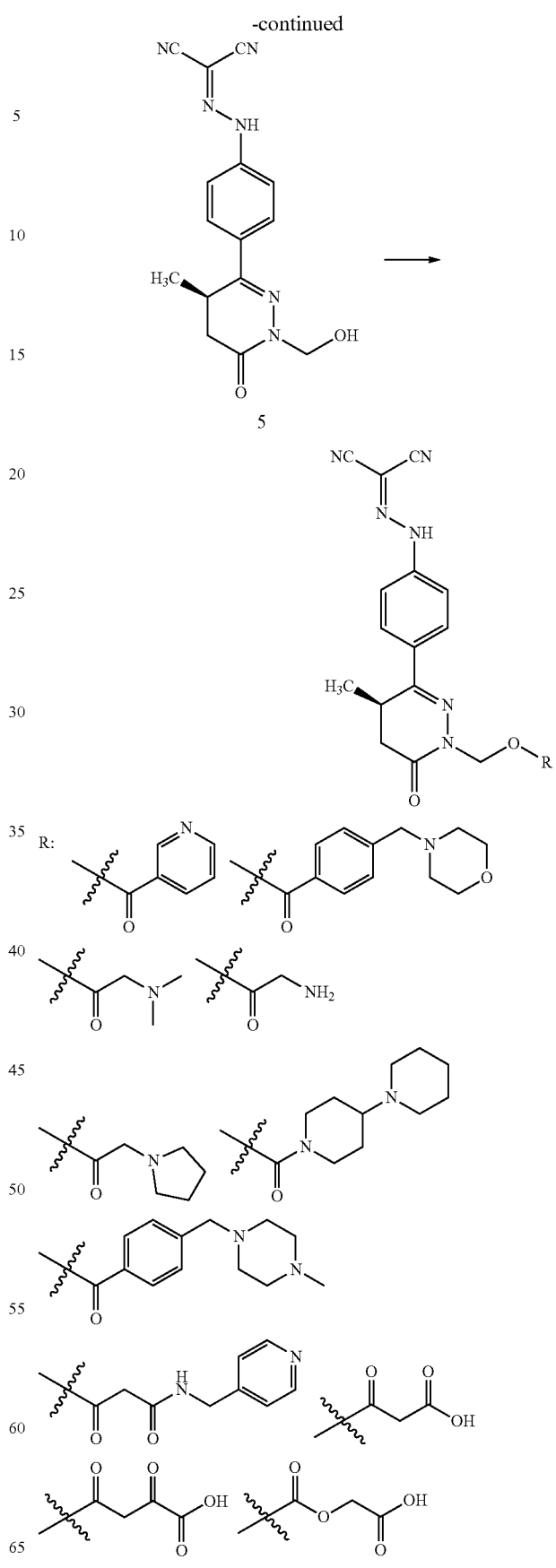

-continued

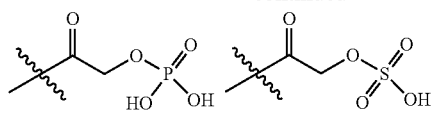

I. Preparation of tert-butyl (R)-(4-((4-methyl-6-oxo-1,4,5,6-tetrahydropyridazin-3-yl)phenyl)carbamate

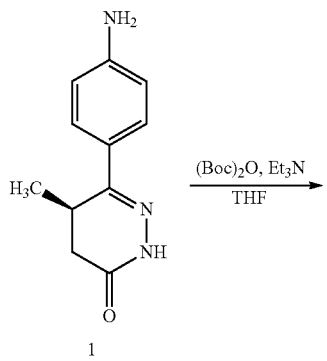

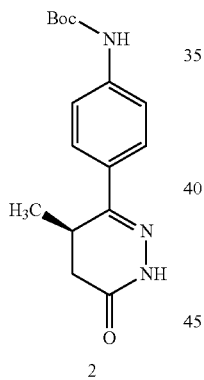

(R)-6-((4-aminophenyl)-5-methyl-4,5-dihydropyridazin-3(2H)-one (101 g, 0.5 mol), di-tert-butyl dicarbonate (163.5 g, 0.75 mol), triethylamine (76 g, 0.75 mol), and tetrahydrofuran (1 L) were added to a 2 L single-necked flask, and stirred at room temperature for 3 days, until no remaining raw materials detectable by TLC detection. The reaction was filtered, and subjected to rotary evaporation under reduced pressure to remove the solvent. Under stirring, petroleum ether (300 mL) was added to the residue, stirred at room temperature for 20 minutes, filtered, and dried, to obtain 84 g of the title compound as a light brown solid (yield: 54%). $^1$H-NMR (400 MHz, DMSO-d$_6$) δ: 10.86 (s, 1H), 9.55 (s, 1H), 7.66-7.70 (m, 2H), 7.50-7.53 (m, 2H), 3.35-3.38 (m, 1H), 2.63-2.69 (m, 1H), 2.18-2.23 (m, 1H), 1.48 (s, 9H), 1.05 (d, 3H, J=7.2 Hz); ESI-MS (m/z): Calcd. For C$_{16}$H$_{21}$N$_3$O$_3$+H: 304.16; Found: 304.17.

II. Preparation of tert-butyl (R)-(4-(1-(hydroxymethyl)-4-methyl-6-oxo-1,4,5,6-tetrahydropyridazin-3-yl)phenyl)carbamate

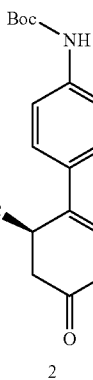

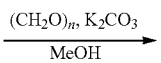

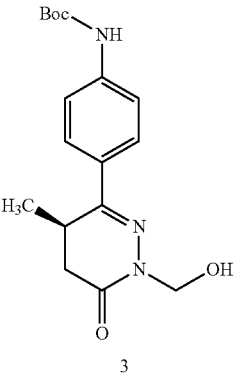

Tert-butyl (R)-(4-((4-methyl-6-oxo-1,4,5,6-tetrahydropyridazin-3-yl)phenyl)carbamate (100 g, 0.33 mol) and methanol (2.5 L) were added to a 3 L three-necked flask, paraformaldehyde (128.2 g, 4.27 mol) and potassium carbonate (95.3 g, 0.69 mol) were added under stirred, and stirred at room temperature overnight. The reaction was completed under TLC monitoring. The solvent was removed by rotary evaporation under reduced pressure. The concentrate was purified by column chromatography (petroleum ether:ethyl acetate, v:v=1:1), to obtain 60.0 g of the title compound as a white solid (yield: 55%). $^1$H-NMR (400 MHz, DMSO-d$_6$) δ: 9.56 (s, 1H), 7.74 (d, 2H, J=8.5 Hz), 7.53 (d, 2H, J=8.5 Hz), 6.13-6.17 (m, 1H), 5.10-5.15 (m, 1H), 4.95-5.00 (m, 1H), 3.35-3.41 (m, 1H), 2.67-2.73 (m, 1H), 2.28-2.33 (m, 1H), 1.48 (s, 9H), 1.06 (d, 3H, J=7.2 Hz); ESI-MS (m/z): Calcd. For C$_{17}$H$_{23}$N$_3$O$_4$+H: 334.17; Found: 334.18.

III. Preparation of (R)-6-((4-aminophenyl)-2-(hydroxymethyl)-5-methyl-4,5-dihydropyridazin-3(2H)-one hydrochloride

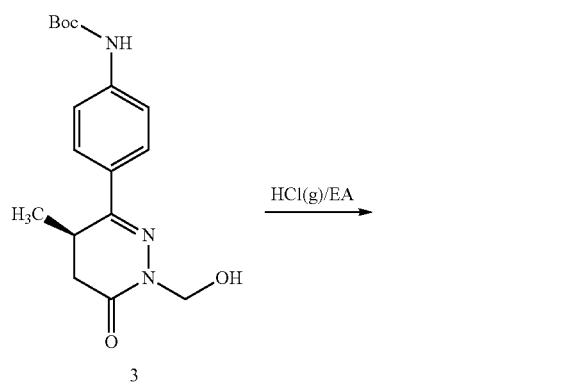

Tert-butyl (R)-(4-((4-methyl-6-oxo-1,4,5,6-tetrahydropyridazin-3-yl)phenyl)carbamate (20 g, 0.06 mol) was added to a 500 mL three-necked flask, and 50 mL of ethyl acetate was added. After stirring at room temperature for 5 minutes, a solution of hydrogen chloride in ethyl acetate (100 mL, 20 wt %) was dropwise added. After dropwise addition, it was stirred at room temperature for 2 hours, and No raw materials remained detectable by TLC detection. The solvent was removed by rotary evaporation under reduced pressure, to obtain 23 g of yellow solid. The crude product was directly subjected to the next reaction.

IV. Preparation of (R)-N-((4-(1-(hydroxymethyl)-4-methyl-6-oxo-1,4,5,6-tetrahydropyridazin-3-yl)phenyl)bis-cyanomethylene)hydrazine

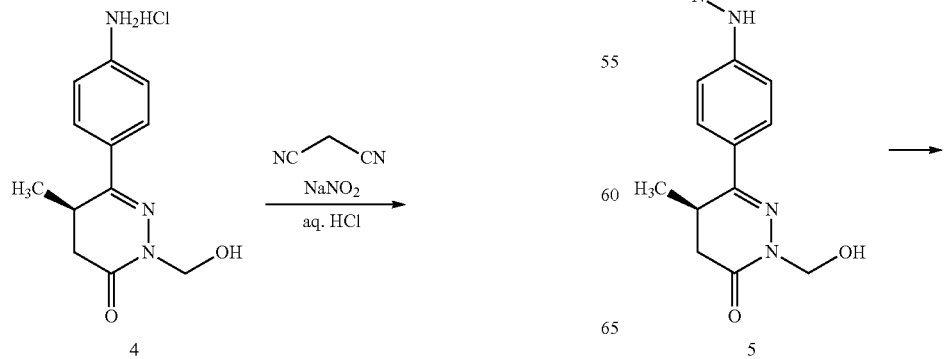

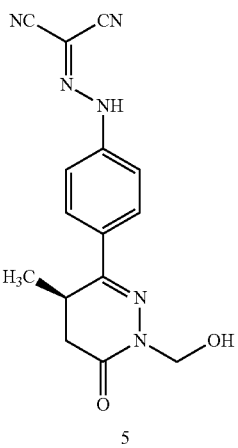

23 g of compound (R)-6-((4-aminophenyl)-2-(hydroxymethyl)-5-methyl-4,5-dihydropyridazin-3(2H)-one hydrochloride obtained in step 3 was transferred into a 2 L flask with 2.6% aqueous solution of hydrochloric acid (500 mL) and cooled in an ice-water bath. At 5~10° C., a solution formed by dissolving 7.05 g of sodium nitrite (0.1 mol) into 50 mL of water was added to the above reaction solution. To 50 mL of water, malononitrile (6.2 g, 0.094 mol) was dissolved, and added to the above reaction solution at 5~10° C. After addition, the ice-water bath was removed. After stirring at room temperature for 2 hours, a 20% aqueous solution of sodium acetate was slowly added, to adjust pH value to 5~6. A yellow suspension was obtained, filtered, washed with water, and dried, to obtain 11.2 g of the title compound as a yellow solid with a two-step yield of 60%. $^1$H-NMR (400 MHz, DMSO-$d_6$) δ: 13.1 (br, s, 1H), 7.88-7.92 (m, 2H), 7.52-7.55 (m, 2H), 5.13 (d, 1H, J=10 Hz), 5.00 (d, 1H, J=10 Hz), 3.37-3.43 (m, 1H), 2.71-2.77 (m, 1H), 2.31-2.35 (m, 1H), 1.08 (d, 3H, J=7.2 Hz); ESI-MS (m/z): Calcd. For $C_{15}H_{14}N_6O_2$+H: 311.12; Found: 311.13.

Example 1: Preparation of (R)-(3-((4-(2-(dicyanomethylene)hydrazino)phenyl)-4-methyl-6-oxo-5,6-dihydropyridazin-1(4H)-yl)methyl nicotinate (TCX-1001-029)

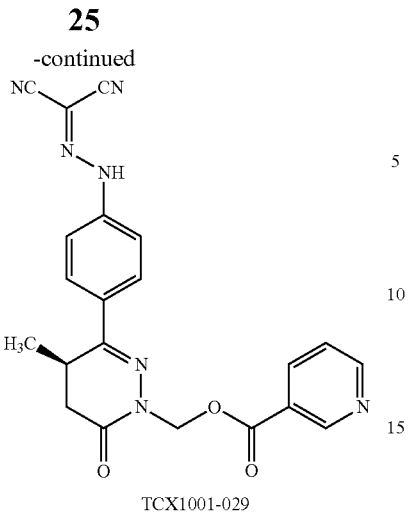

TCX1001-029

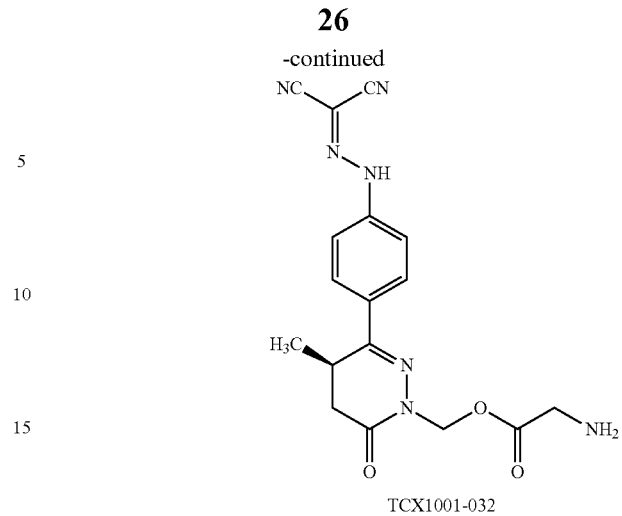

TCX1001-032

The compound (R)-N-((4-(1-(hydroxymethyl)-4-methyl-6-oxo-1,4,5,6-tetrahydropyridazin-3-yl)phenyl)biscyanomethylene)hydrazine (0.26 g, 0.84 mmol), TSTU (0.3 g, 1 mmol), and nicotinic acid (0.11 g, 0.92 mmol) were added to a 50 mL single-necked flask, 5 mL of dichloromethane was added, then triethylamine (0.3 g, 3 mmol) was added under stirring, and stirred at room temperature for 5 hours. After no remaining raw materials were detectable by TLC detection, the solvent was removed by rotary evaporation under reduced pressure. The resulting concentrate was purified by Pre-HPLC (eluent: DCM/MeOH, v:v=50/1), to obtain 0.12 g of the title compound as a yellow solid (yield: 34%). $^1$H-NMR (400 MHz, DMSO-$d_6$) δ: 13.1 (br, s, 1H), 9.08 (s, 1H), 8.83-8.85 (m, 1H), 8.27-8.30 (m, 1H), 7.90-7.92 (m, 2H), 7.54-7.60 (m, 3H), 5.98-6.08 (m, 2H), 3.50-3.54 (m, 1H), 2.91-2.97 (m, 1H), 2.51-2.53 (m, 1H), 1.13 (d, 3H, J=7.2 Hz); ESI-MS (m/z): Calcd. For $C_{21}H_{17}N_7O_3$+H: 416.14; Found: 416.15.

Example 2: Preparation of (R)-3-((4-(2-(dicyanomethylene)hydrazino)phenyl)-4-methyl-6-oxo-5,6-dihydropyridazin-1(4H)-yl)methyl glycinate (TCX-1001-032)

The compound (R)-N-((4-(1-(hydroxymethyl)-4-methyl-6-oxo-1,4,5,6-tetrahydropyridazin-3-yl)phenyl)biscyanomethylene)hydrazine (0.2 g, 0.64 mmol), glycine (0.12 g, 1.6 mmol), 1-(3-dimethylaminopropyl)-3-ethylcarbodiimide (0.31 g, 1.6 mmol), 4-dimethylpyridine (0.08 g, 0.64 mmol), and 5 mL of N,N-dimethylacetamide were successively added to a 50 mL single-necked flask, and stirred at room temperature overnight. The solvent was removed by rotary evaporation under reduced pressure, and the concentrate was purified by column chromatography (eluent: DCM/MeOH, v:v=30/1), to obtain 70 mg of the title compound as a yellow solid (yield: 30%). $^1$H-NMR (400 MHz, DMSO-$d_6$) δ: 13.2 (br, s, 1H), 7.75-7.81 (m, 2H), 7.36-7.41 (m, 2H), 5.95-6.05 (m, 2H), 3.48-3.54 (m, 1H), 3.17-3.23 (m, 2H), 2.95-3.02 (m, 1H), 2.67-2.69 (m, 1H), 1.14 (d, 3H, J=7.2 Hz); ESI-MS (m/z): Calcd. For $C_{19}H_{21}N_7O_3$+H: 368.14; Found: 368.15.

Example 3: Preparation of (R)-(3-((4-(2-(dicyanomethylene)hydrazino)phenyl)-4-methyl-6-oxo-5,6-dihydropyridazin-1(4H)-yl)methyl 2-pyrrolidin-1-yl-acetate (TCX-1001-039)

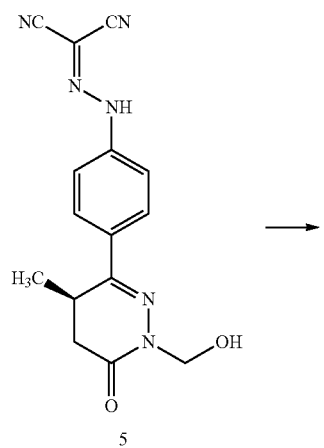

→

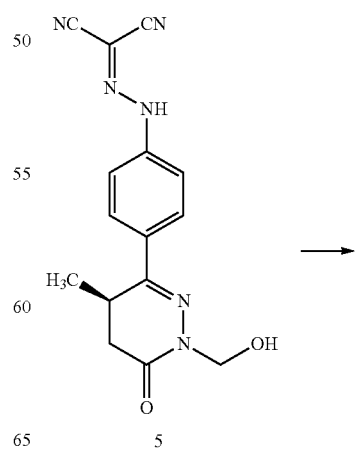

→

27

-continued

TCX1001-039

28

-continued

TCX1001-030

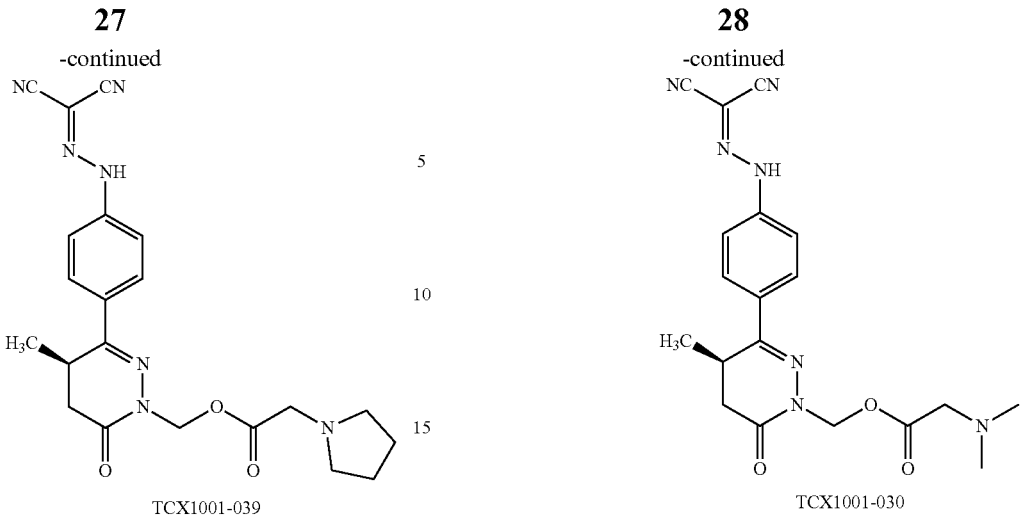

The compound (R)-N-((4-(1-(hydroxymethyl)-4-methyl-6-oxo-1,4,5,6-tetrahydropyridazin-3-yl)phenyl)biscyanomethylene)hydrazine (300 mg, 0.97 mmol), 2-(pyrrolidin-1-yl)acetic acid hydrochloride (321 mg, 1.94 mmol), EDCI (465 mg, 2.43 mmol), and DMAP (118 mg, 0.97 mmol) were dissolved in DMA (10 mL), and stirred at room temperature for 18 hours. To the system, ethyl acetate (10 mL) and water (10 mL) were added, stirred, and separated. The organic phase was washed with water (3×10 mL), and dried over anhydrous sodium sulfate. The solvent was removed by rotary evaporation under reduced pressure, and the crude product was purified by Pre-HPLC, to obtain 210 mg of the title compound as a yellow solid product (yield: 51.3%). $^1$H-NMR (400 MHz, DMSO-$d_6$) δ: 13.0 (br, s, 1H), 7.80-7.74 (m, 2H), 7.38-7.33 (m, 2H), 6.05-5.95 (m, 2H), 3.52-3.46 (m, 1H), 3.35(s, 2H), 3.02-2.95 (m, 1H), 2.68-2.66 (m, 1H), 2.61-2.58 (m, 2H), 1.72-1.70 (m, 2H), 1.13 (d, 3H, J=7.2 Hz); ESI-MS (m/z): Calcd. For $C_{20}H_{20}N_7O_3$+H: 407.16; Found: 407.217.

Example 4: Preparation of (R)-(3-((4-(2-(dicyanomethylene)hydrazino)phenyl)-4-methyl-6-oxo-5,6-dihydropyridazin-1(4H)-yl)methyl N,N-dimethylglycinate (TCX-1001-030)

The compound (R)-N-((4-(1-(hydroxymethyl)-4-methyl-6-oxo-1,4,5,6-tetrahydropyridazin-3-yl)phenyl)biscyanomethylene)hydrazine (0.2 g, 0.64 mmol), N,N-dimethylglycinate (0.16 g, 1.6 mmol), 1-(3-dimethylaminopropyl)-3-ethylcarbodiimide (0.31 g, 1.6 mmol), 4-dimethylpyridine (0.08 g, 0.64 mmol), and 5 mL of N,N-dimethylacetamide were successively added to a 50 mL single-necked flask, and stirred at room temperature overnight. The solvent was removed by rotary evaporation under reduced pressure, and the concentrate was purified by column chromatography (eluent: DCM/MeOH, v:v=30/1), to obtain 0.06 g of the title compound as a yellow solid (yield: 24%). $^1$H-NMR (400 MHz, DMSO-$d_6$) δ: 13.0 (br, s, 1H), 7.74-7.80 (m, 2H), 7.33-7.38 (m, 2H), 5.95-6.05 (m, 2H), 3.46-3.52 (m, 1H), 3.19-3.25 (m, 2H), 2.95-3.02 (m, 1H), 2.75-2.85 (m, 6H), 2.66-2.68 (m, 1H), 1.13 (d, 3H, J=7.2 Hz); ESI-MS (m/z): Calcd. For $C_{19}H_{21}N_7O_3$+H: 396.17; Found: 396.18.

Example 5: Preparation of (R)-(3-((4-(2-(dicyanomethylene)hydrazino)phenyl)-4-methyl-6-oxo-5,6-dihydropyridazin-1(4H)-yl)methyl 4-(morpholin-1-ylmethyl)benzoate (TCX-1001-031)

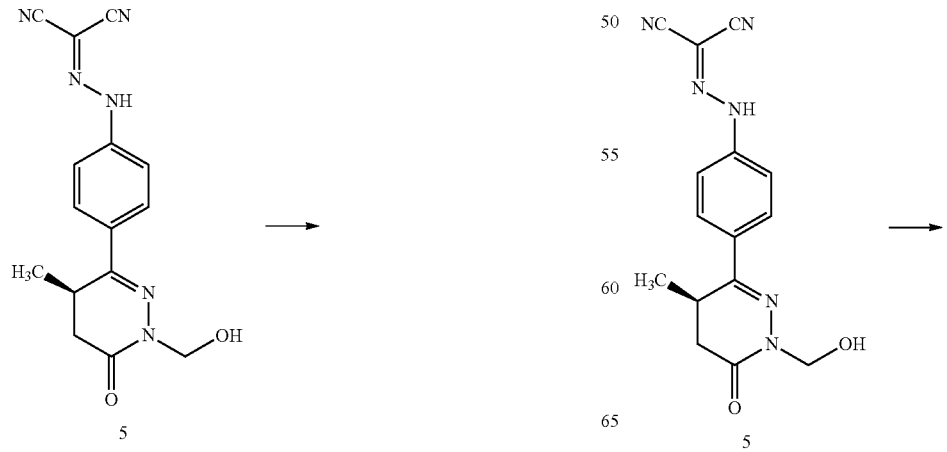

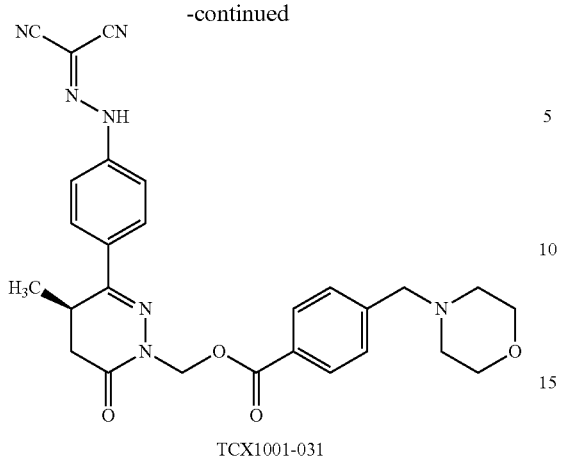

TCX1001-031

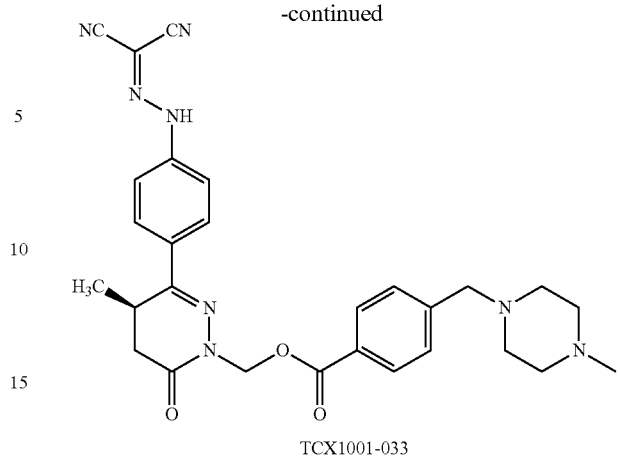

TCX1001-033

The compound (R)-N-((4-(1-(hydroxymethyl)-4-methyl-6-oxo-1,4,5,6-tetrahydropyridazin-3-yl)phenyl)biscyanomethylene)hydrazine (0.2 g, 0.64 mmol) was dissolved in 2 mL of pyridine, then 4-chloromethylbenzoyl chloride (0.22 g, 1.16 mmol) was added, and stirred at room temperature for 2 hours. The reaction solution was diluted with 30 mL of ethyl acetate. Then the organic phase was successively washed with distilled water and saturated brine, dried over anhydrous sodium sulfate, and spin-dried. The resulting concentrate was dissolved in DMF (3 mL), sodium iodide (0.05 g) was added, followed by morpholine (0.13 g, 1.5 mmol), and stirred at room temperature overnight. The solvent was removed by rotary evaporation under reduced pressure, and the resulting concentrate was purified by column chromatography (eluent: DCM/MeOH, v:v=70/1), to obtain 0.11 g of the title compound as a yellow solid (yield: 33%). $^1$H-NMR (400 MHz, DMSO-d$_6$) δ: 13.1 (br, s, 1H), 7.95-8.03 (m, 2H), 7.77-7.83 (m, 2H), 7.53-7.63 (m, 2H), 7.38-7.42 (m, 2H), 5.92-6.06 (m, 2H), 3.56-4.51 (m, 6H), 3.35-3.53 (m, 2H), 2.71-3.15 (m, 4H), 2.41-2.46 (m, 1H), 1.13 (d, 3H, J=7.2 Hz); ESI-MS (m/z): Calcd. For C$_{27}$H$_{27}$N$_7$O$_4$+H: 514.21; Found: 514.22.

Example 6: Preparation of (R)-(3-((4-(2-(dicyanomethylene)hydrazino)phenyl)-4-methyl-6-oxo-5,6-dihydropyridazin-1(4H)-yl)methyl 4-((4-methylpiperazin-1-yl)methyl)benzoate (TCX-1001-033)

The compound (R)-N-((4-(1-(hydroxymethyl)-4-methyl-6-oxo-1,4,5,6-tetrahydropyridazin-3-yl)phenyl)biscyanomethylene)hydrazine (0.2 g, 0.64 mmol) was dissolved in 2 mL of pyridine, then 4-chloromethylbenzoyl chloride (0.22 g, 1.16 mmol) was added, and stirred at room temperature for 2 hours. The reaction solution was diluted with 30 mL of ethyl acetate, then successively washed with distilled water and saturated brine. The organic phase was dried over anhydrous sodium sulfate, and the solvent was removed by rotary evaporation under reduced pressure. The concentrate was dissolved in DMF (3 mL), sodium iodide (0.05 g) was added, followed by N-methylpiperazine (0.15 g, 1.5 mmol), and stirred at room temperature overnight. The solvent was removed by rotary evaporation under reduced pressure, and the concentrate was purified by column chromatography (eluent: DCM/MeOH, v:v=30/1), to obtain 0.05 g of the title compound as a yellow solid (yield: 15.0%). $^1$H-NMR (400 MHz, DMSO-d$_6$) δ: 13.2 (br, s, 1H), 7.95-7.88 (m, 2H), 7.83-7.78 (m, 2H), 7.59-7.54 (m, 2H), 7.33-7.29 (m, 2H), 6.06-5.90 (m, 2H), 3.70-3.58 (m, 2H), 3.52-3.48 (m, 1H), 3.43-3.27 (m, 5H), 3.04-2.98 (m, 1H), 2.93-2.80 (m, 3H), 2.69 (s, 3H), 2.47-2.41 (m, 1H), 1.13 (d, 3H, J=7.2 Hz); ESI-MS (m/z): Calcd. For C$_{27}$H$_{27}$N$_7$O$_4$+H: 527.12; Found: 526.80.

Example 7: Preparation of (R)-(3-((4-(2-(dicyanomethylene)hydrazino)phenyl)-4-methyl-6-oxo-5,6-dihydropyridazin-1(4H)-yl)methyl 4-(piperidin-1-yl)piperidin-1-ylformate (TCX-1001-037)

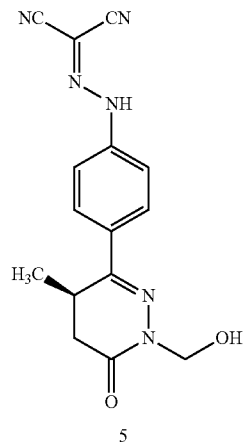

→

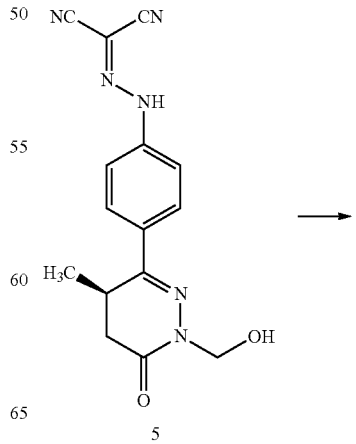

→

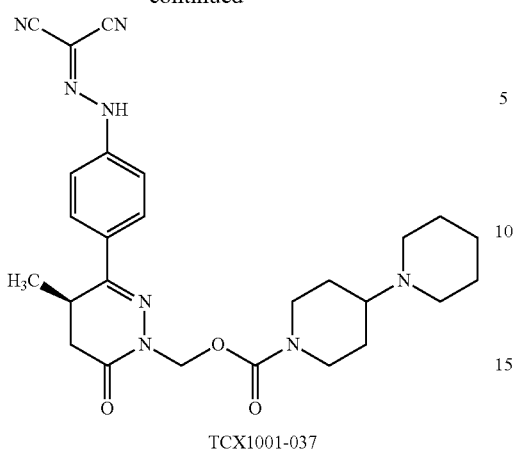

TCX1001-037

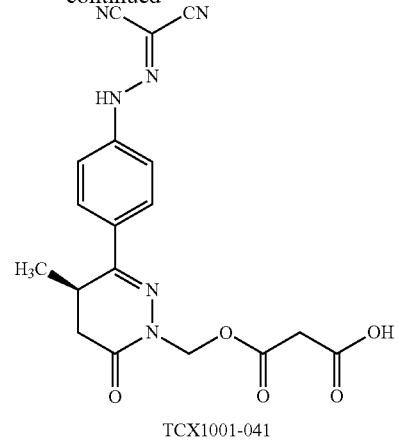

TCX1001-041

10 mL of anhydrous tetrahydrofuran, 1.24 g of (R)-N-((4-(1-(hydroxymethyl)-4-methyl oxo-1,4,5,6-tetrahydropyridazin-3-yl)phenyl)biscyanomethylene)hydrazine, 0.71 g of N,N'-carbonyldiimidazole, and 0.67 g of 4-piperidylpiperidine were successively added to a 50 mL single-necked flask, stirred at room temperature for 48 hours, and the reaction was completed by TLC monitoring (developer: dichloromethane/methanol=10/1). The solvent was removed by rotary evaporation under reduced pressure, and the concentrate was purified by column chromatography (eluent: DCM/MeOH, v:v=30/1), to obtain 0.50 g of the title compound as a yellow solid (yield: 24.8%). $^1$H-NMR (400 MHz, DMSO-$d_6$) δ: 12.35 (s, 1H), 7.76-7.80 (d, 2H), 7.40-7.43 (d, 2H), 5.94-6.02 (m, 2H), 4.25 (m, 2H), 3.43-3.49 (d, 1H), 2.70-2.76 (d, 3H), 2.60-2.65 (d, 1H), 2.5 (t, 4H), 2.3-2.45 (m, 1H), 1.8 (m, 2H), 1.51-1.65 (m, 4H), 1.3-1.5 (m, 4H), 1.08-1.14 (d, 3H); ESI-MS (m/z): Calcd. For $C_{26}H_{32}N_8O_3$+H: 505.6; Found: 505.61.

Example 8: Preparation of (R)-(3-((4-(2-(dicyanomethylene)hydrazino)phenyl)-4-methyl-6-oxo-5,6-dihydropyridazin-1(4H)-yl)methyl 2-carboxyl acetate (TCX-1001-041)

Malonic acid (0.21 g, 2.06 mmol), triethylamine (0.36 mL, 2.6 mmol), DMAP (13 mg, 0.1 mmol), and isopropenyl chloroformate (0.08 mL, 0.73 mmol) were successively added to 10 mL of dichloromethane. After cooling to 0° C. in an ice-water bath, a solution of (R)-N-((4-(1-(hydroxymethyl)-4-methyl-6-oxo-1,4,5,6-tetrahydropyridazin-3-yl)phenyl)biscyanomethylene) hydrazine (0.16 g, 0.52 mmol) in dichloromethane (10 mL) was added. The reaction solution was stirred at 0° C. for 2 hours, then poured into 3 mL of 10% aqueous acetic acid solution, and stirred at room temperature for 0.5 hours. The reaction solution was successively washed with distilled water and saturated brine, and the organic phase was dried over anhydrous sodium sulfate. The solvent was removed by rotary evaporation under reduced pressure, and the concentrate was purified by column chromatography (dichloromethane/methanol/formic acid, v:v:v=20/1/0.05), to obtain 80 mg of the title compound as a yellow solid (yield: 39.0%). $^1$H-NMR (400 MHz, DMSO-$d_6$) δ: 14.1 (br, s, 1H), 13.1 (br, s, 1H), 7.90-7.92 (m, 2H), 7.54-7.60 (m, 2H), 5.98-6.08 (m, 2H), 3.55-3.60 (m, 1H), 3.4 (s, 2H), 2.91-2.97 (m, 1H), 2.51-2.53 (m, 1H), 1.13 (d, 3H, J=7.2 Hz); ESI-MS (m/z): Calcd. For $C_{21}H_{17}N_7O_3$+H: 397.12; Found: 397.15.

Example 9: Preparation of (R)-(3-((4-(2-(dicyanomethylene)hydrazino)phenyl)-4-methyl-6-oxo-5,6-dihydropyridazin-1(4H)-yl)methyl 3-carboxylpropionate (TCX-1001-034)

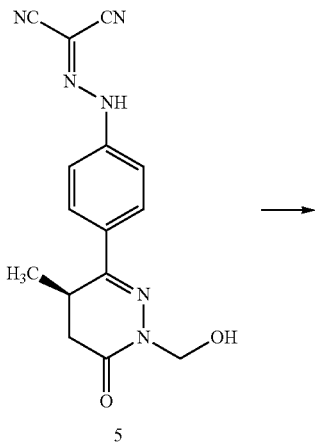

→

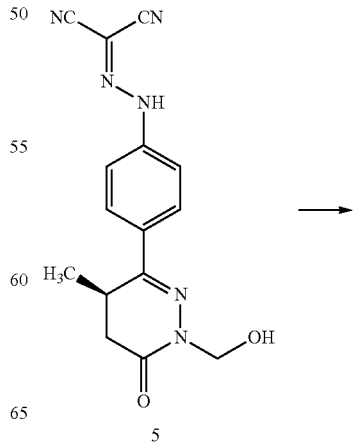

→

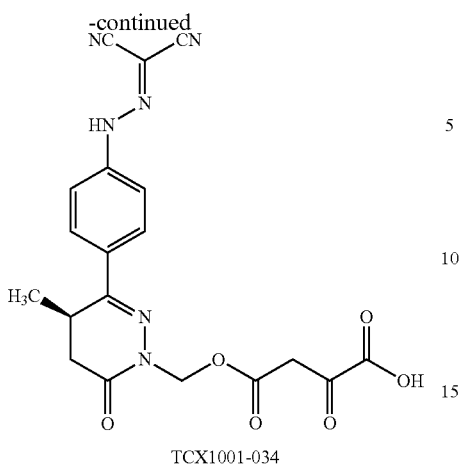

TCX1001-034

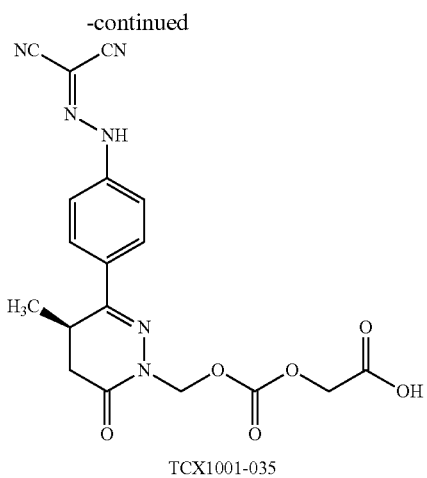

TCX1001-035

Succinic acid (0.488 g, 4.12 mmol), triethylamine (0.72 mL, 5.2 mmol), 4-dimethylaminopyridine (DMAP) (26 mg, 0.2 mmol), and isopropenyl chloroformate (0.16 mL, 1.46 mmol) were dissolved in 10 mL of dichloromethane. After cooling to 0° C. in an ice-water bath, a solution of (R)-N-((4-(1-(hydroxymethyl)-4-methyl-6-oxo-1,4,5,6-tetrahydropyridazin-3-yl)phenyl)biscyanomethylene) hydrazine (0.32 g, 1.04 mmol) in dichloromethane (10 mL) was added. The reaction solution was stirred at 0° C. for 2 hours, then poured into 3 mL of 10% aqueous acetic acid solution, and stirred at room temperature for 0.5 hours. The reaction solution was successively washed with distilled water and saturated brine, and the organic phase was dried over anhydrous sodium sulfate. The solvent was removed by rotary evaporation under reduced pressure, and the concentrate was purified by column chromatography (dichloromethane/methanol/formic acid, v:v:v=20/1/0.05), to obtain 0.14 g of the title compound as a yellow solid (yield: 33%). $^1$H-NMR (400 MHz, DMSO-d$_6$) δ: 14.3 (br, s, 1H), 13.4 (br, s, 1H), 7.91-7.93 (m, 2H), 7.55-7.61 (m, 2H), 5.99-6.10 (m, 2H), 3.51-3.54 (m, 1H), 2.91-2.97 (m, 1H), 2.75-2.51 (m, 5H), 1.13 (d, 3H, J=7.2 Hz); ESI-MS m/z: Calcd. For $C_{21}H_{17}N_7O_3$+H: 411.14; Found: 411.15.

Example 10: Preparation of (R)-(3-((4-(2-(dicyanomethylene)hydrazino)phenyl) methyl-6-oxo-5,6-dihydropyridazin-1(4H)-yl)methyl carboxylmethyl-oxyformate (TCX-1001-035)

(R)-N-((4-(1-(hydroxymethyl)-4-methyl-6-oxo-1,4,5,6-tetrahydropyridazin-3-yl)phenyl)biscyanomethylene)hydrazine (0.16 g, 0.52 mmol), N,N'-carbonyldiimidazole (CDI) (95 mg, 0.57 mmol), and 2-hydroxyacetic acid (40 mg, 0.57 mmol) were dissolved in 5 mL of THF, stirred at room temperature for 48 hours, and the reaction was completed by TLC monitoring. The solvent was removed by rotary evaporation under reduced pressure, and the concentrate was purified by column chromatography (dichloromethane/methanol/formic acid, v:v:v=20/1/0.05), to obtain 60 mg of the title compound as a yellow solid (yield: 28%). $^1$H-NMR (400 MHz, DMSO-d$_6$) δ: 14.1 (br, s, 1H), 13.1 (br, s, 1H), 7.90-7.92 (m, 2H), 7.56-7.61 (m, 2H), 5.97-6.08 (m, 2H), 5.2 (s, 2H), 3.50-3.54 (m, 1H), 2.91-2.97 (m, 1H), 2.52-2.54 (m, 1H), 1.14 (d, 3H, J=7.2 Hz); ESI-MS (m/z): Calcd. For $C_{21}H_{17}N_7O_3$+H: 413.14; Found: 413.15.

Example 11: Preparation of (R)-(3-((4-(2-(dicyanomethylene)hydrazino)phenyl)-4-methyl-6-oxo-5,6-dihydropyridazin-1(4H)-yl)methyl phosphoryloxy-acetate (TCX-1001-040)

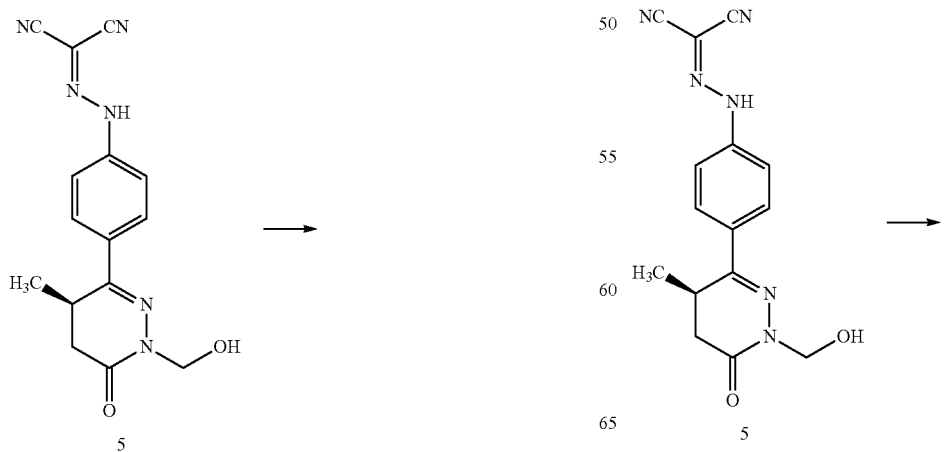

35

-continued

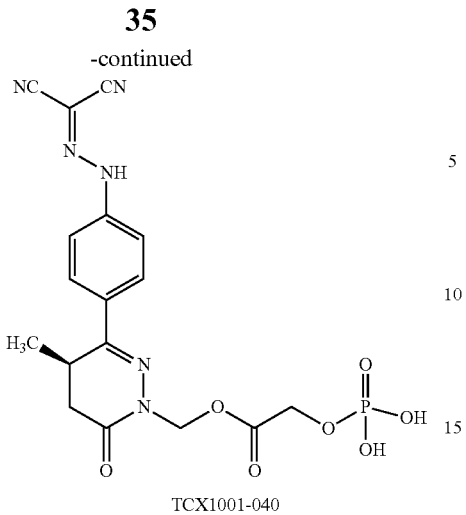

TCX1001-040

(R)-N-((4-(1-(hydroxymethyl)-4-methyl-6-oxo-1,4,5,6-tetrahydropyridazin-3-yl)phenyl)biscyanomethylene)hydrazine (0.26 g, 0.84 mmol), TSTU (0.3 g, 1 mmol), and (phosphoryloxy)acetic acid (0.16 g, 1 mmol) were added to a 50 mL single-necked flask, 5 mL of dichloromethane was added, then triethylamine (0.3 g, 3 mmol) was added under stirring, and stirred at room temperature for 15 hours. No raw materials remained detectable by TLC detection. The solvent was removed by rotary evaporation under reduced pressure, and the concentrate was separated by Pre-HPLC, to obtain 0.11 g of the title compound, as a yellow solid (yield: 29%). $^1$H-NMR (400 MHz, DMSO-$d_6$) δ: 13.1 (br, s, 1H), 7.90-7.92 (m, 2H), 7.54-7.60 (m, 2H), 5.98-6.08 (m, 2H), 5.7 (br, s, 2H), 4.3 (s, 2H), 3.50-3.54 (m, 1H), 2.91-2.97 (m, 1H), 2.51-2.53 (m, 1H), 1.13 (d, 3H, J=7.2 Hz); ESI-MS (m/z): Calcd. For $C_{21}H_{17}N_7O_3$+H: 449.0; Found: 449.10.

Example 12: Preparation of (R)-(3-((4-(2-(dicyanomethylene)hydrazino)phenyl)-4-methyl-6-oxo-5,6-dihydropyridazin-1(4H)-yl)methyl sulfonyloxyacetate (TCX-1001-038)

36

-continued

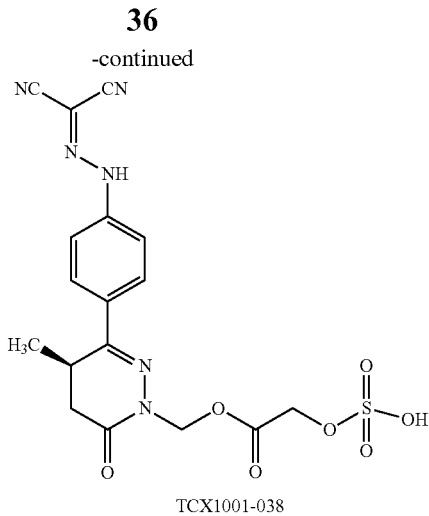

TCX1001-038

(R)-N-((4-(1-(hydroxymethyl)-4-methyl-6-oxo-1,4,5,6-tetrahydropyridazin-3-yl)phenyl)biscyanomethylene)hydrazine (0.52 g, 1.68 mmol), TSTU (0.6 g, 2 mmol), and (sulfonyloxy)acetic acid (0.32 g, 2 mmol) were added to a 50 mL single-necked flask, 15 mL of dichloromethane was added, followed by triethylamine (0.6 g, 6 mmol), and stirred at room temperature for 15 hours. No raw materials remained detectable by TLC monitoring. The solvent was removed by rotary evaporation under reduced pressure, and the concentrate was separated by Pre-HPLC, to obtain 0.15 g of the title compound as a yellow solid (yield: 20%). $^1$H-NMR (400 MHz, DMSO-$d_6$) δ: 15.1 (br, s, 1H), 13.1 (br, s, 1H), 7.90-7.92 (m, 2H), 7.54-7.60 (m, 2H), 5.98-6.08 (m, 2H), 4.2 (s, 2H), 3.52-3.56 (m, 1H), 2.91-2.97 (m, 1H), 2.52-2.54 (m, 1H), 1.13 (d, 3H, J=7.2 Hz); ESI-MS (m/z): Calcd. For $C_{21}H_{17}N_7O_3$+H: 449.08; Found: 449.10.

Example 13: Preparation of (R)-(3-((4-(2-(dicyanomethylene)hydrazino)phenyl) methyl-6-oxo-5,6-dihydropyridazin-1(4H)-yl)methyl 3-oxo-3-((pyridinylmethyl)amino)propionate (TCX-1001 -036)

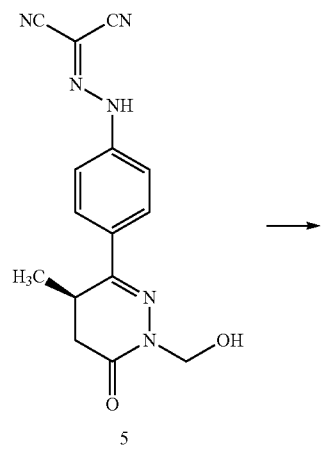

⟶

(1) Preparation of ethyl 3-oxo-3-((pyridin-4-ylmethyl)amino)propionate

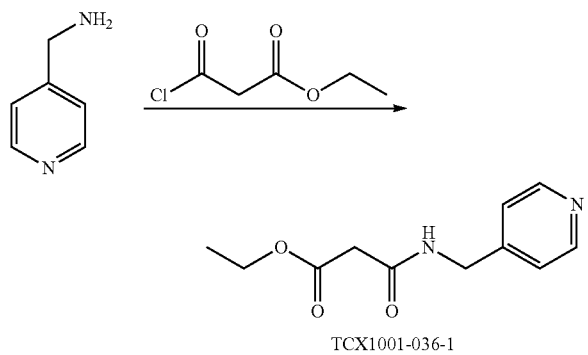

TCX1001-036-1

Ethyl chloroformylacetate (5.8 mL, 46.23 mmol) and 4-pyridinylmethylamine (5 g, 46.23 mmol) were dissolved in 200 mL of THF. The reaction solution was cooled to 0° C., then triethylamine (9.5 mL, 69.35 mmol) was slowly dropwsie added. After dropwise addition, the reaction solution was stirred at room temperature for 2 hours, and the reaction was completed by TLC monitoring. The solvent was removed by rotary evaporation under reduced pressure, the concentrate was dissolved in 200 mL of ethyl acetate, washed with distilled water and saturated brine successively, and the organic phase was dried over anhydrous sodium sulfate. The solvent was removed by rotary evaporation under reduced pressure, and the concentrate was purified by column chromatography (dichloromethane/methanol, v:v=50/1), to obtain 5 g of the target product ethyl 3-oxo-3-((pyridin-4-ylmethyl)amino)propionate as a brown solid (yield: 48%). $^1$H-NMR (400 MHz, CDCl$_3$) δ: 8.57-8.55 (m, 1H), 8.13-8.10 (m, 2H), 7.35-7.30 (m, 2H), 4.62-4.60 (m, 2H), 4.26-4.18 (m, 2H), 3.4 (s, 2H), 1.32-1.37 (t, 3H, J=7.2 Hz); ESI-MS (m/z): Calcd. For C$_{21}$H$_{17}$N$_7$O$_3$+H: 223.10; Found: 222.90.

(2) Preparation of 3-oxo-3-((pyridin-4-ylmethyl)amino)propanoic acid

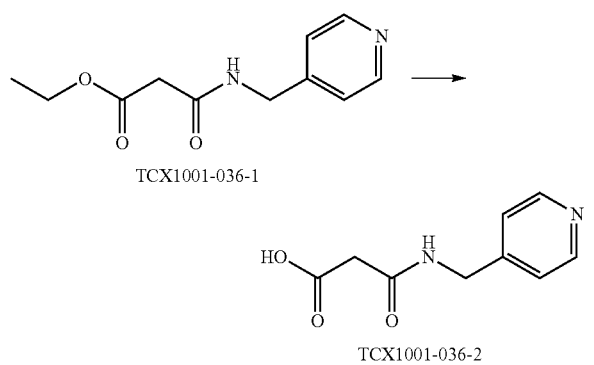

The compound ethyl 3-oxo-3-((pyridin-4-ylmethyl)amino)propionate (2.2 g, 10 mmol) was dissolved in a mixed solvent of 10 mL methanol, 10 mL THF, and 5 mL water, and lithium hydroxide monohydrate (0.84 g, 20 mmol) was added. The reaction solution was stirred at room temperature for 16 hours, and the reaction was completed by TLC monitoring. The solvent was removed by rotary evaporation under reduced pressure. The system was diluted with 10 mL of water, adjusted with 3N HCl aqueous solution to adjust to pH 5~6, then extracted with ethyl acetate (20 mL×3), and the organic phases were combined. The organic phase was successively washed with distilled water and saturated brine, and dried over anhydrous sodium sulfate. The solvent was removed by rotary evaporation under reduced pressure, and the concentrate was purified by column chromatography (dichloromethane/methanol/formic acid, v:v:v=20/1/0.05), to obtain 1.5 g of target product 3-oxo-3-((pyridin-4-ylmethyl)amino)propionic acid (yield: 77%). $^1$H-NMR (400 MHz, DMSO-d$_6$) δ: 13.1 (br, s, 1H), 8.67-8.65 (m, 1H), 8.18-8.16(m, 2H), 7.40-7.35 (m, 2H), 4.62-4.60 (m, 2H), 3.4 (s, 2H); ESI-MS (m/z): Calcd. For C$_{21}$H$_{17}$N$_7$O$_3$+H: 195.07; Found: 195.10.

(3) Preparation of (R)-(3-((4-(2-(dicyanomethylene)hydrazino)phenyl)-4-methyl-6-oxo-5,6-dihydropyridazin-1 (4H)-yl)methyl 3-oxo-3-((pyridin-4-ylmethyl)amino)propionate (TCX-1001-0361)

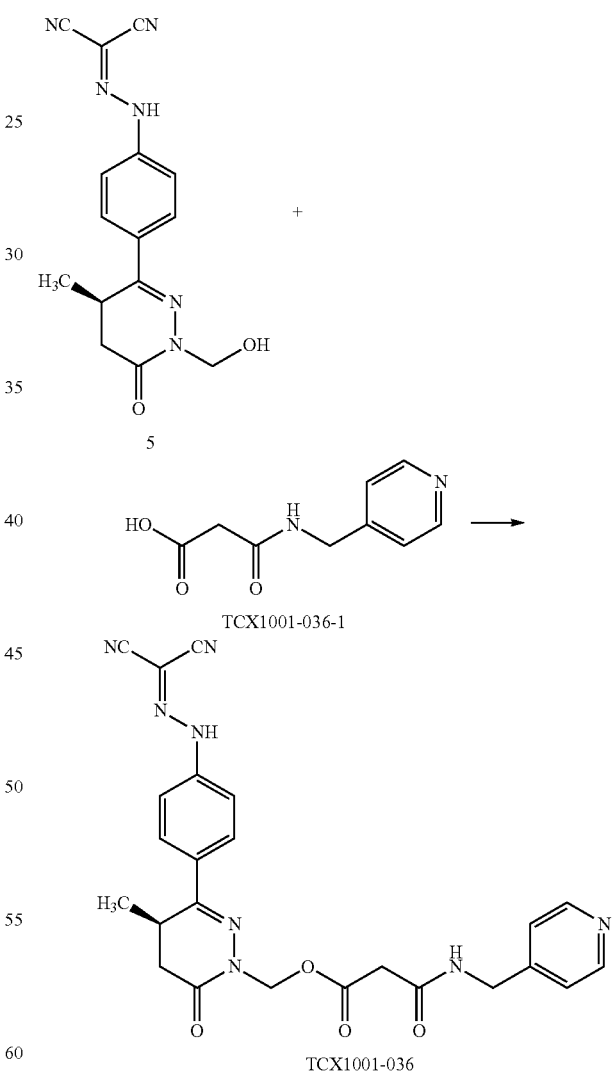

The compound (R)-N-((4-(1-(hydroxymethyl)-4-methyl-6-oxo-1,4,5,6-tetrahydropyridazin-3-yl)phenyl)biscyanomethylene)hydrazine (0.26 g, 0.84 mmol), TSTU (0.3 g, 1 mmol), and 3-oxo-3-((pyridin-4-ylmethyl)amino)propanoic acid (0.18 g, 0.92 mmol) were added to a 50 mL single-necked flask, 5 mL of dichloromethane was added, then triethylamine (0.3 g, 3 mmol) was added under stirring, and stirred at room temperature for 5 hours. After no remaining raw materials were detectable by TLC detection, the solvent was removed by rotary evaporation under reduced pressure. The resultant was purified by column chromatography (eluent: DCM/MeOH, v:v=50/1), to obtain 0.11 g of the title compound as a yellow solid (yield: 27%). $^1$H-NMR (400 MHz, DMSO-$d_6$) δ: 13.2 (br, s, 1H), 8.71-8.68 (m, 1H), 8.32-8.29 (m, 2H), 7.95-7.93 (m, 2H), 7.65-7.62 (m, 2H), 7.45-7.40 (m, 2H), 6.08-5.98 (m, 2H), 4.62-4.60 (m, 2H), 3.54-3.50 (m, 1H), 3.4 (s, 2H), 2.98-2.92 (m, 1H), 2.53-2.51 (m, 1H), 1.15 (d, 3H, J=7.2 Hz); ESI-MS (m/z): Calcd. For $C_{21}H_{17}N_7O_3$+H: 487.14; Found: 487.15.

The present invention solves the problem of poor solubility of levosimendan in most solvents (including water). When preparing a liquid formulation of levosimendan, the defects of having to use an organic solvent and adding a toxic co-solvent at the same time are avoided.

Meanwhile, due to the solubility limitation of levosimendan itself, it is difficult to make oral formulations. The novel compounds designed and prepared in the invention solve this defect and can be dispersed in water, that is, they can be dispersed in gastric juice or intestinal juice in the form of molecules or ions, which is beneficial to the oral absorption in organisms, and can solve the problem that it is difficult to prepare levosimendan into oral formulations.

Example 14: Sample Stability Test

After the compound samples prepared in Examples 1-13 above were placed (in naked form) for 10 days under conditions of strong light (4500Lx±500Lx) irradiation, high temperature (60° C.±2° C.) and high humidity (90%±5%), there were no obvious changes in appearance and related substances. Thus, the compound samples prepared in Examples 1-13 are stable through preliminary investigation.

Example 15: Sample Characterization Experiment

The chromatographic conditions for detection were as follows: octadecylsilane-bonded silica gel was used as the filler; phosphate buffer (1.56 g of sodium dihydrogen phosphate was weighted, 1000 ml of water was added for dissolution, and pH was adjusted to 3.5 with phosphoric acid)-methanol (30:70) was used as the mobile phase; the flow rate was 1.0 mL per minute; the column temperature was 30° C.; the detection wavelength was 254 nm; and the injection volume was 10 μL.

Test solution: an appropriate amount of the product (TCX-H1001-031) was accurately weighted, and dissolved in methanol to make a solution containing 0.5 mg of sample per 1 ml.

The test solution was accurately weighted, and injected into a liquid chromatograph, to record the chromatogram.

Figure 2:
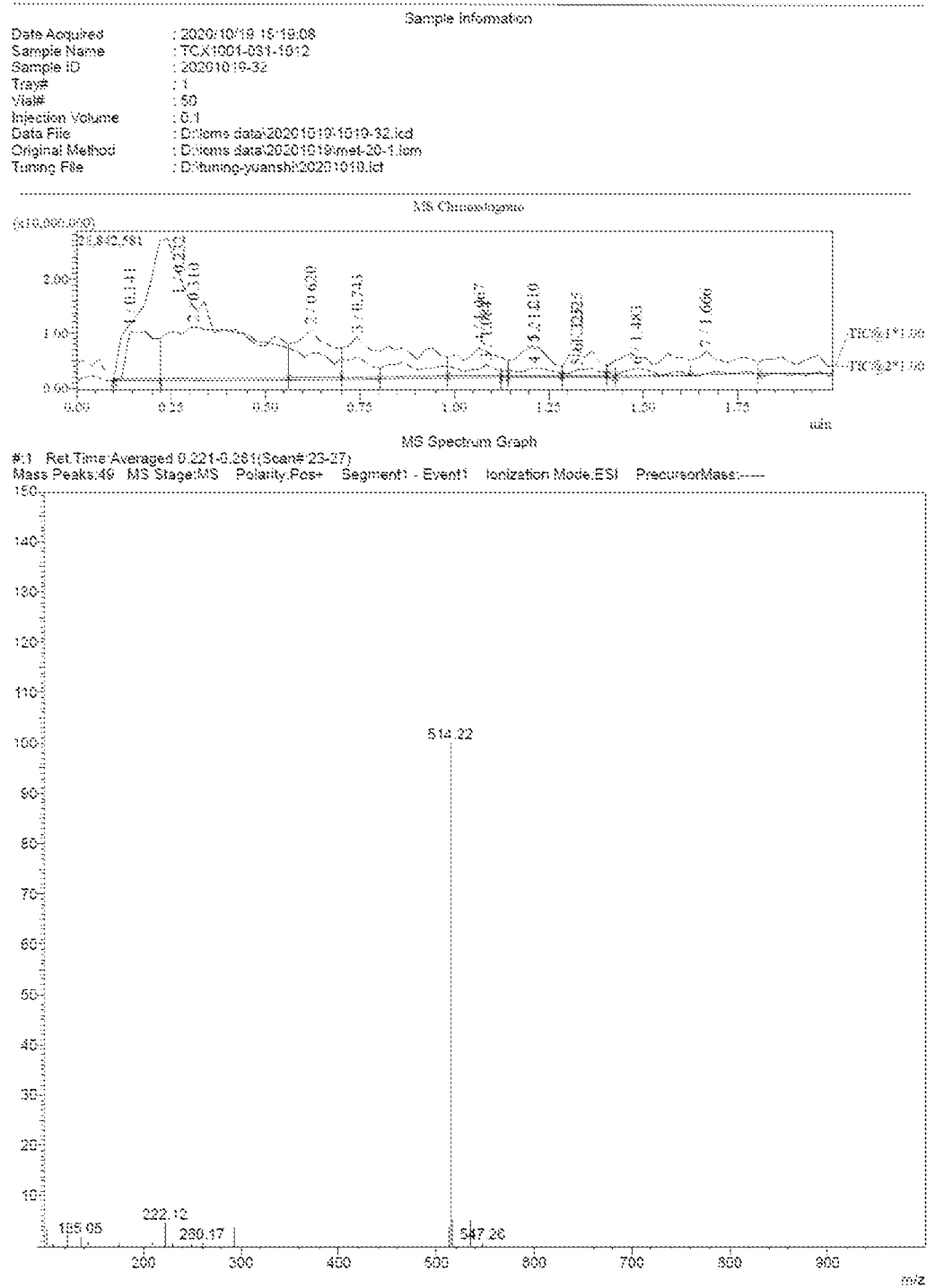
FIG. 2 ESI-MS spectrum of compound TCX1001-031.
Figure 3:
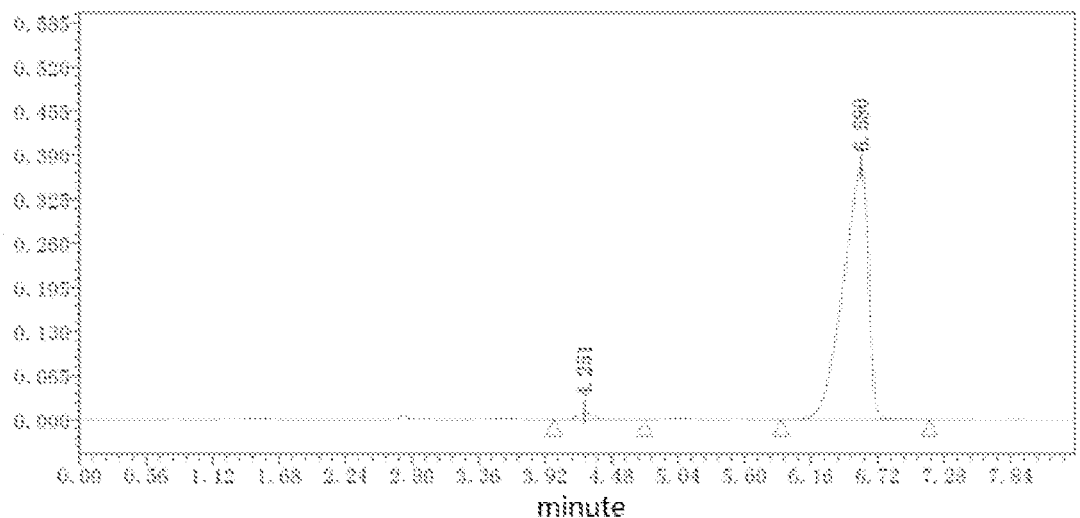
FIG. 3 Liquid chromatogram of compound TCX1001-031.

FIGS. 1-3 are $^1$H-NMR spectrum, ESI-MS spectrum, and liquid chromatogram of compound TCX-H1001-031 prepared in Example 5, respectively.

Example 16: Pharmacokinetic Study for Compound

Figure 4:
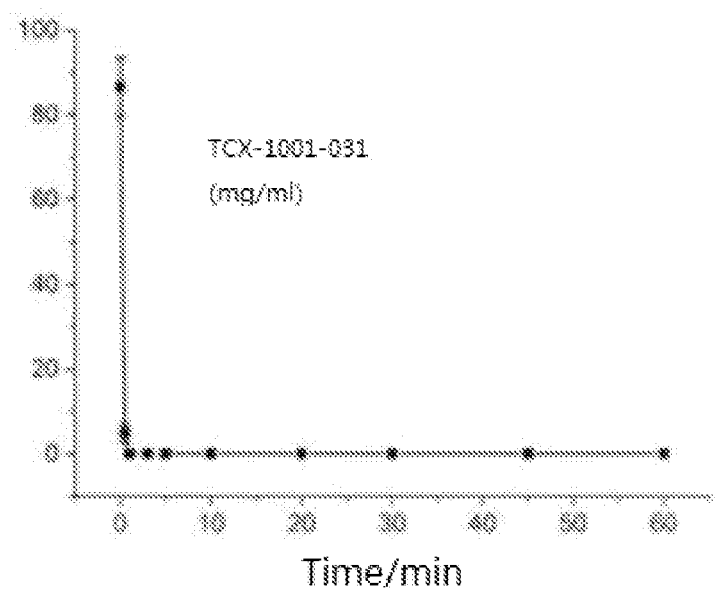
FIG. 4 Change profile of the content of compound TCX1001-031 itself in the pharmacokinetic study.
Figure 5:
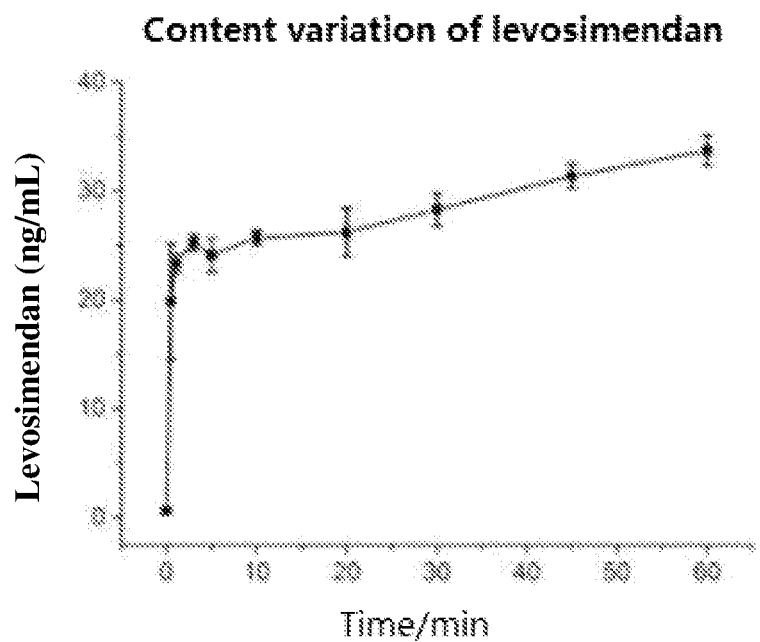
FIG. 5 Change profile of the content of released levosimendan in the pharmacokinetic study of compound TCX1001-031.
Figure 6:
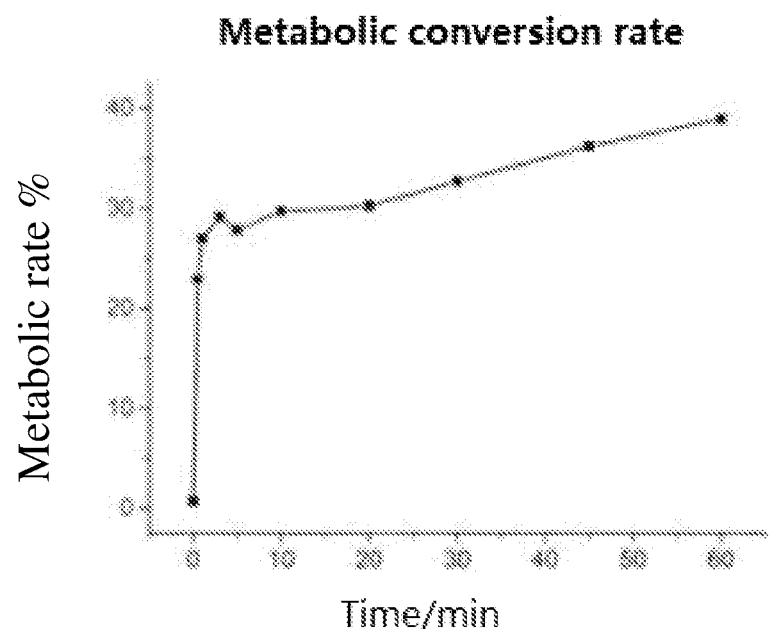
FIG. 6 Metabolic conversion rate of compound TCX1001-031 in the pharmacokinetic study.

FIGS. 4-6 are the change profile of the content of compound TCX1001-031 itself in plasma after administration in the pharmacokinetic study, the change profile of the content of released levosimendan, and the pharmacokinetic metabolic conversion rate, respectively. It can be seen from the figures that TCX-1001-031 can be completely metabolized within 1 minute, that is, its content drops to 0 within 1 minute; while the content of the original drug levosimendan released by the metabolism begins to increase rapidly, and then gradually increases, and becomes completely stable with the prodrug metabolism, indicating that the metabolic conversion rate of TCX-1001-031 into the raw material within 10 minutes is about 40%, and it is a high-quality prodrug molecule.

Table 3 shows the results of in vivo administration of some specific compounds of present invention, indicating that they are completely metabolized within 1-10 minutes respectively, and the content of levosimendan increases accordingly, and it is stable with the completion of the prodrug metabolism. The conversion rates of these compounds to levosimendan in plasma within 10 minutes are approximately 30-45%.

TABLE 3

| Metabolic conversion rate | |
|---|---|
| Compound | Metabolic conversion rate |
| 1 (TCX1001-029) | 39.4% |
| 2 (TCX1001-031) | 40.0% |
| 3 (TCX1001-032) | 35.1% |
| 4 (TCX1001-030) | 38.9% |
| 5 (TCX1001-037) | 35.6% |
| 6 (TCX1001-033) | 44.6% |
| 7 (TCX1001-036) | 36.9% |
| 8 (TCX1001-039) | 35.1% |
| 9 (TCX1001-041) | 35.6% |
| 10 (TCX1001-034) | 34.9% |
| 11 (TCX1001-035) | 37.8% |
| 12 (TCX1001-040) | 37.6% |
| 13 (TCX1001-038) | 36.4% |

From the results of the pharmacokinetic study, among the metabolic conversion rates of 13 prodrug molecules in plasma within 10 minutes, the metabolic conversion rates of Compounds 1, 2, 4, and 6 are the highest. According to current data, the above-mentioned 13 compound molecules all have the potential to serve as prodrugs.

The Examples only represent several embodiments of the invention, and the descriptions thereof are more specific and detailed, but should not be construed as a limitation to the scope of the invention. It should be pointed out that for those skilled in the art, without departing from the concept of the invention, some alterations and modifications can also be made, which all fall into the scope of the invention. Thus, the scope of the invention is defined by the appended claims.

What is claimed is:

1. A prodrug compound of levosimendan, characterized in that, the compound is a compound as shown by formula I, and solvates, hydrates, N-oxides, stereoisomers, and pharmaceutically acceptable salts thereof;

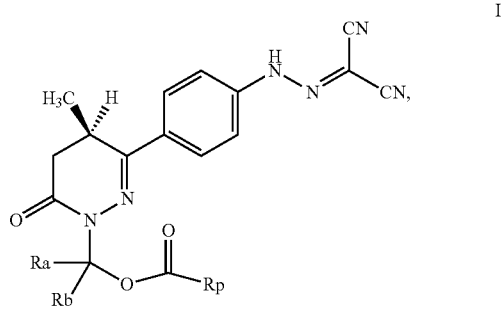

wherein each of Ra and Rb is selected from hydrogen atom or C1-C6 alkyl; and

Rp is selected from a basic group containing N atom or an acidic group containing carboxyl group, phosphate group, sulfate group or sulfonate group.

2. The prodrug compound according to claim 1, characterized in that, each of Ra and Rb is hydrogen atom.

3. The prodrug compound according to claim 2, characterized in that, the basic group containing N atom is selected from 4-(morpholin-1-ylmethyl)phenyl, 4-(4-methylpiperazin-1-ylmethyl)phenyl, N,N-dimethylaminomethyl, pyridin-3-yl, 4-(piperidin-1-yl)-piperidin-1-yl, aminomethyl, pyridin-4-ylmethylaminoformylmethyl, or pyrrolidin-1-ylmethyl.

4. The prodrug compound according to claim 2, characterized in that, the acidic group is selected from carboxylmethyl, carboxylethyl, carboxylmethoxy, phosphoryloxymethyl, sulfonyloxymethyl, sulfonylmethyl, phosphoryloxyethyl, sulfonyloxyethyl, or sulfonylethyl.

5. The prodrug compound according to claim 3, characterized in that, the basic group containing N atom is selected from 4-(morpholin-1-ylmethyl)phenyl, 4-(4-methylpiperazin-1ylmethyl)phenyl, and N,N-dimethylaminomethyl, or pyridin-3-yl.

6. The prodrug compound according to claim 4, characterized in that, the acidic group is selected from carboxylmethyl, carboxyl ethyl, phosphoryloxymethyl, sulfonyloxymethyl, or sulfonylmethyl.

7. The prodrug compound according to claim 5, characterized in that, the basic group containing N atom is selected from 4-(morpholin-1-ylmethyl)phenyl or 4-(4-methylpiperazin-1-ylmethyl)phenyl.

8. Use of the prodrug compound according to any one of claims 1 to 7 in the manufacture of a medicament for treating heart failure diseases.

* * * * *